US008614082B2

(12) United States Patent
Frolov et al.

(10) Patent No.: US 8,614,082 B2
(45) Date of Patent: Dec. 24, 2013

(54) ATTENUATION OF ENCEPHALITOGENIC ALPHAVIRUS AND USES THEREOF

(75) Inventors: Ilya V. Frolov, Galveston, TX (US); Elena Frolova, Galveston, TX (US); Scott C. Weaver, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/284,098

(22) Filed: Oct. 28, 2011

(65) Prior Publication Data
US 2012/0100181 A1 Apr. 26, 2012

Related U.S. Application Data

(62) Division of application No. 12/228,710, filed on Aug. 15, 2008, now abandoned.

(60) Provisional application No. 60/964,969, filed on Aug. 16, 2007.

(51) Int. Cl.
*C12N 7/04* (2006.01)
*A61K 39/12* (2006.01)

(52) U.S. Cl.
USPC .............................. 435/236; 424/218.1; 435/5

(58) Field of Classification Search
None
See application file for complete search history.

(56) References Cited

PUBLICATIONS

Perera et al., Journal of Virology, 2001, 75(1):1-10.*
Garmashova et al., Journal of Virology, 2007 (published ahead of print on Nov. 15, 2006), 81(5):2472-2484.*

* cited by examiner

*Primary Examiner* — Stacey B. Chen

(57) ABSTRACT

The present invention is drawn to generating attenuated and less cytopathic forms of New World alphaviruses that can be used in immunogenic compositions as vaccines against both Old and New World alphaviruses. In this regard, the present invention discloses that the N-terminal, ~35-aa-long peptide of VEEV, EEEV and, most likely, of WEEV capsid proteins plays the most critical role in the downregulation of cellular transcription and development of cytopathic effect. The identified, VEEV-specific peptide, $C_{VEE}30$-$68$, includes two domains with distinguished functions. The integrity of both domains determines not only the intracellular distribution of $C_{VEE}$, but is also essential for direct capsid function in the inhibition of transcription. The replacement of the N-terminal fragment of $C_{VEE}$ by its SINV-specific counterpart in VEEV TC-83 genome does not affect virus replication in vitro, but makes it less cytopathic and more attenuated in vivo.

11 Claims, 22 Drawing Sheets

VEErepL/GFP/Pac                    CFU/µg of RNA

| Cap | nsP1 | nsP2 | nsP3 | nsP4 | GFP | Pac | p(A) |    $2.5\text{-}3.2 \times 10^5$ VEErepL/C$_{VEE}$110GFP/Pac

| Cap | nsP1 | nsP2 | nsP3 | nsP4 | C K$_{110}$ | GFP | Pac | p(A) |    $1.1\text{-}3.0 \times 10^2$ VEErepL/C$_{VEE}$80GFP/Pac

| Cap | nsP1 | nsP2 | nsP3 | nsP4 | C G$_{80}$ | GFP | Pac | p(A) |    $3.0\text{-}3.8 \times 10^2$

```
VEE 30 TDPFLAMQVQELTRSMANLTFKQR*RDAPPEGPSAKKPKK 68
                                          SEQ ID NO: 1
EEE 33 FR-P--A-IED-R--I----L----*APN--A--P--R*--  70
                                          SEQ ID NO: 2
SIN 34 ARNG--S-I-Q--TAVSA-VIG-AT-PQ--RPRPPPRQ--  73
                                          SEQ ID NO: 3
SFV 34 VPD-Q-Q-M-Q-ISAVNA--MR-N*AI--ARP-KP--K-T  72
                                          SEQ ID NO: 4
```

| Construct | CFU/µg of RNA |
|---|---|
| VEErepL/C$_{VEE}$68GFP/Pac — Cap-nsP1-nsP2-nsP3-nsP4-C$K_{68}$-GFP-Pac-p(A) | 3.6–6.6 × 10$^2$ |
| VEErepL/C$_{VEE}$60GFP/Pac — Cap-nsP1-nsP2-nsP3-nsP4-C$G_{60}$-GFP-Pac-p(A) | 3.4–4.4 × 10$^5$ |
| VEErepL/C$_{VEE}$33GFP/Pac — Cap-nsP1-nsP2-nsP3-nsP4-C$F_{33}$-GFP-Pac-p(A) | 3.7–4.2 × 10$^5$ |
| VEErepL/GFP/Pac — Cap-nsP1-nsP2-nsP3-nsP4-GFP-Pac-p(A) | 3.9–5.1 × 10$^5$ |

```
                              SEQUENCE LISTING

<160> NUMBER OF SEQ ID NOS: 5

<210> SEQ ID NO 1
<211> LENGTH: 39
<212> TYPE: PRT
<213> ORGANISM: Alphavirus

<400> SEQUENCE: 1

Thr Asp Pro Phe Leu Ala Met Gln Val Gln Glu Leu Thr Arg Ser Met
1               5                   10                  15

Ala Asn Leu Thr Phe Lys Gln Arg Arg Asp Ala Pro Pro Glu Gly Pro
            20                  25                  30

Ser Ala Lys Lys Pro Lys Lys
        35

<210> SEQ ID NO 2
<211> LENGTH: 38
<212> TYPE: PRT
<213> ORGANISM: Alphavirus

<400> SEQUENCE: 2

Phe Arg Pro Pro Leu Ala Ala Gln Ile Glu Asp Leu Arg Arg Ser Ile
1               5                   10                  15

Ala Asn Leu Thr Leu Lys Gln Arg Ala Pro Asn Pro Pro Ala Gly Pro
            20                  25                  30

Pro Ala Lys Arg Lys Lys
        35

<210> SEQ ID NO 3
<211> LENGTH: 40
<212> TYPE: PRT
<213> ORGANISM: Alphavirus

<400> SEQUENCE: 3

Ala Arg Asn Gly Leu Ala Ser Gln Ile Gln Gln Leu Thr Thr Ala Val
1               5                   10                  15

Ser Ala Leu Val Ile Gly Gln Ala Thr Arg Pro Gln Pro Pro Arg Pro
            20                  25                  30

Arg Pro Pro Pro Arg Gln Lys Lys
        35                  40
```

-continued

```
<210> SEQ ID NO 4
<211> LENGTH: 39
<212> TYPE: PRT
<213> ORGANISM: Alphavirus

<400> SEQUENCE: 4

Val Pro Asp Phe Gln Ala Gln Gln Met Gln Gln Leu Ile Ser Ala Val
1               5                   10                  15

Asn Ala Leu Thr Met Arg Gln Asn Ala Ile Ala Pro Ala Arg Pro Pro
            20                  25                  30

Lys Pro Lys Lys Lys Thr
        35

<210> SEQ ID NO 5
<211> LENGTH: 12
<212> TYPE: PRT
<213> ORGANISM: Artificial Sequence
<220> FEATURE:
<223> OTHER INFORMATION: synthetic linker sequence for fusion protein

<400> SEQUENCE: 5

Gly His Gly Thr Gly Ser Gly Gly Ser Gly Ser Ser
1               5                   10
```

ATTENUATION OF ENCEPHALITOGENIC ALPHAVIRUS AND USES THEREOF

CROSS-REFERENCE TO RELATED APPLICATIONS

This application claims priority to and is a divisional of U.S. patent application Ser. No. 12/228,710 filed Aug. 15, 2008 (abandoned), which claims priority to U.S. Provisional Application No. 60/964,969 filed Aug. 16, 2007 (expired). The entire contents of each above-referenced disclosure are incorporated herein by reference in their entirety.

FEDERAL FUNDING LEGEND

This invention was produced using funds obtained through National Institutes of Health grant AI057156 and Public Health Service grant AI050537. Consequently, the Federal government has certain rights in this invention.

BACKGROUND OF THE INVENTION

1. Field of the Invention

The present invention relates generally to the field of virology and vaccine development. More specifically, the present invention provides a method to attenuate encephalitogenic alphaviruses including but not limited to VEEV, EEEV and WEEV. The attenuated phenotype is irreversible and thus, can be effective as human and/or veterinary vaccines in immunogenic composition(s).

2. Description of the Related Art

The Alphavirus genus in the Togaviridae family includes a number of important human and animal pathogens (15). Alphaviruses are currently classified into 6 antigenic complexes and are widely distributed both in the New and the Old World. They are efficiently transmitted by mosquitoes, in which they cause a persistent, lifelong infection that does not noticeably affect biological functions of the vectors. In vertebrates, the infection is acute and characterized by high-titer viremia, rash and fever and encephalitis until the death of the infected host or clearance of the virus by the immune system. The encephalitogenic alphaviruses, including Venezuelan (VEEV), eastern (EEEV) and western equine encephalitis (WEEV) viruses, represent a continuous public health threat in the U.S. (40, 47-49). They circulate in the Central, South and North Americas and have an ability to cause fatal disease in humans and horses. During VEEV epizootics, equine mortality can reach 83%, and, in humans, this virus produces a severe temporary immunodeficiency and a greatly debilitating and sometimes fatal disease (41). The overall mortality rate is below 1%, but the neurological disease, including disorientation, ataxia, mental depression, and convulsions, can be detected in up to 14% of all infected individuals, especially children (23). Sequelae of VEEV-related clinical encephalitis in humans are also described (10, 27).

The VEEV genome is represented by a single-stranded RNA molecule of positive polarity of almost 12-kb. It mimics the structure of cellular mRNA, in which it contains a Cap at the 5' terminus and a poly(A) tail at the 3' end of the RNA. VEEV genome has been cloned in a cDNA form (24) that allows a wide variety of genetic manipulation to be undertaken.

The current experimental vaccine against VEEV infection was developed four decades ago by serial passaging of the virulent, subtype IAB Trimidad Donkey (TRD) VEEV strain in guinea pig heart cell cultures (3). Presently, TC-83 is still the only available vaccine for laboratory workers and military personnel. Over 8,000 humans have been vaccinated during the past 4 decades (2, 6, 36), and the cumulative data unambiguously demonstrated that nearly 40% of vaccinated people develop a disease with some symptoms typical of natural VEEV infection, including a febrile, systemic illness and other adverse effects (2, 3, 21). No effective antivirals have been developed against this virus as well.

In spite of the continuous threat of VEEV epidemics, the biology of this virus has been studied less intensively than that of other, less pathogenic alphaviruses, such as Sindbis (SINV) and Semliki Forest (SFV) viruses. This situation can be partially explained by the fact that for a long time, it was believed that the latter viruses represent excellent models for studying the mechanism of alphavirus replication, virus-host interactions and encephalitis development (14). However, very strong differences in pathogenesis and the severity of the caused diseases suggest that this may not exactly be the case. Moreover, the results from recent comparative studies with the Old World alphaviruses (SINV and SFV) and the New World alphaviruses (VEEV and EEEV) (1, 9, 11-13, 35, 45) demonstrated that both of these groups have developed the ability to interfere with cellular transcription and use it as a means of downregulating cellular antiviral reactions. However, the mechanism of transcription inhibition appears to be fundamentally different, and while the Old World alphaviruses use nsP2 to inhibit cellular transcription (11), the more encephalitogenic VEEV and EEEV use their capsid protein for the same function (1, 12). Expression of the latter protein by different vectors is sufficient for induction of cell death and cytopathic effect (CPE) in tissue culture, and this effect strongly correlates with the inhibition of transcription of cellular messenger and ribosomal RNAs. Moreover, the replacement of structural genes in VEEV by those derived from SINV made the chimeric virus strongly less cytopathic and incapable of interfering with the development of an antiviral reaction developing in the cells having no defect in IFN-a/b induction and signaling (12).

Despite this, prior art is deficient in an immunogenic composition(s) that will prevent and treat infection caused by encephalitogenic alphavirus. The current invention fulfils this long standing need in the art.

SUMMARY OF THE INVENTION

In one embodiment of the present invention, there is provided a method of attenuating a New World encephalitogenic alphavirus comprising: mutating one or more than one amino acids in the amino terminus of the capsid protein of the alphavirus or replacing the entire capsid protein or amino terminus of the capsid protein of the alphavirus by capsid protein or amino terminus of less pathogenic Old World alphavirus.

In a related embodiment of the present invention, there is provided an immunogenic composition, comprising the attenuated New World encephalitogenic alphavirus generated by the method described supra.

In another related embodiment of the present invention, there is provided a method of preventing an infection caused by Old and New World encephalitogenic alphavirus in a subject, comprising: administering an immunologically effective amount of the immunogenic composition described supra to the subject.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

Figures 1A, 1B:
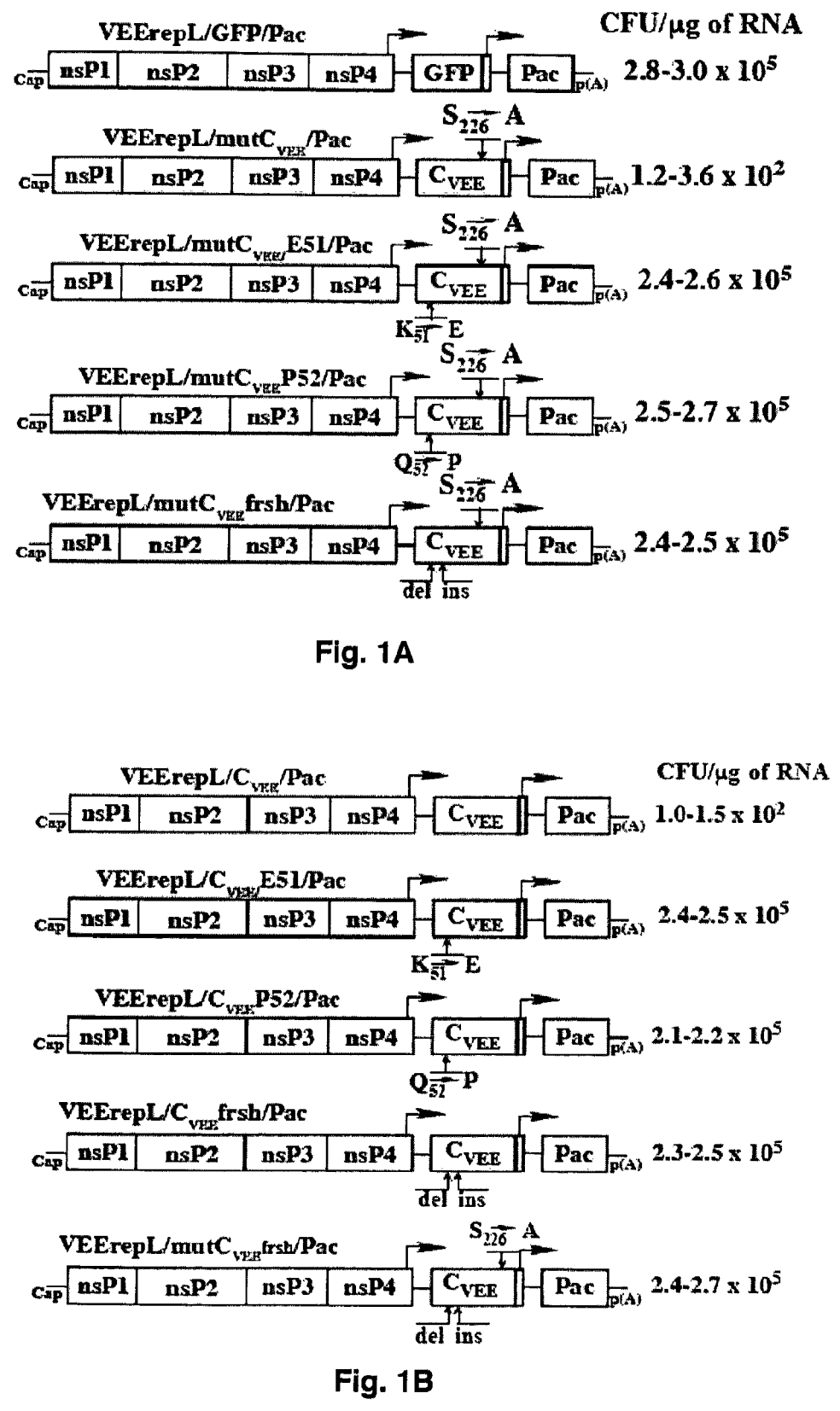

FIGS. 1A-1F show the effect of expression of capsid mutants on cellular transcription and cell growth and the ability of cells to form PurR foci. FIGS. 1A and 1B are schematic representations of VEEV replicons expressing GFP or mutated capsids. Arrows indicate positions of the subgenomic promoters. Replicons expressed either CVEE with mutated protease (mutCVEE) (FIG. 1A) or CVEE having no mutations in protease domain (FIG. 1B). VEErepL/CVEEfrsh/Pac was included in FIGS. 1B, 1D and 1F as an additional control. Different dilutions of the electroporated cells were seeded into 100-mm tissue culture dishes and Puromycin selection performed. PurR cell colonies were stained with crystal violet at 4-9 days post-transfection, depending on their growth rates. The results are presented in colony-forming units (CFU) per mg of RNA used for transfection. The ranges indicate variations between the experiments. FIGS. 1C and 1D compare growth of the cells transfected with VEEV replicons expressing GFP, and different capsids. Equal numbers of cells were seeded into 6-well Costar plates. Puromycin selection (10 mg/ml) was performed between 6 and 48 h post transfection. Then cells were incubated in puromycin-free media, and viable cells were counted at the indicated times. The data were normalized on the number of viable adherent cells determined at 6 h post transfection. FIGS. 1E and 1F show analysis of cellular transcription. RNA labeling was performed with [$^3$H]uridine at 24 post transfection for 2 h. RNA samples were analyzed by gel electrophoresis. For quantitative analysis, the aliquots of the RNA samples used for the gel were washed on the Whatman 3MM filters with TCA and the radioactivity was measured by liquid scintillation counting. Error bars indicate variations between parallel samples.

FIGS. 2A-2C show effect of the C-terminal deletions in capsid on cellular transcription and cell viability. FIG. 2A is a schematic representation of VEEV genome-based replicons expressing the amino terminal fragments of $C_{VEE}$, fused with GFP, and analysis of their ability to establish persistent replication and develop Pur$^R$ foci. Arrows indicate the positions of the subgenomic promoters. Numbers indicate the last capsid-specific amino acid. FIG. 2B compares growth of cells carrying VEEV replicons expressing GFP or indicated fusions. FIG. 2C shows inhibition of transcription in the BHK-21 cells transfected with VEEV replicons expressing indicated proteins. Cells were electroporated by 5 mg of the in vitro-synthesized RNAs. At 24 h post-transfection, cellular RNAs were labeled with [$^3$H]uridine in the absence of ActD for 2 h and analyzed by RNA gel electrophoresis. Quantitative analysis of residual cellular transcription was performed as described in FIG. 1. Error bars indicate variations between parallel samples.

FIGS. 3A-3D show effect of the N-terminal VEEV capsid fragment on cellular transcription and cell viability. FIG. 3A shows sequence alignment of $C_{VEE}$30-68 peptide (SEQ ID NO: 1) with the corresponding capsid fragment of other alphaviruses. VEEV, Venezuelan equine encephalitis virus; EEEV, eastern equine encephalitis virus (SEQ ID NO: 2); SINV, Sindbis virus (SEQ ID NO: 3); SFV, Semliki Forest virus (SEQ ID NO: 4). Helix I sequences are indicated in red. Residues identical to those in the VEEV sequence are indicated by dashes. Stars indicate positions of the deletions introduced for better alignment of the sequences. FIG. 3B is a schematic representation of VEEV genome-based replicons expressing the amino terminal fragments of $C_{VEE}$, fused with GFP, and analysis of their ability to establish persistent replication and develop PurR foci. Arrows indicate the positions of the subgenomic promoters. Numbers indicate the last capsid-specific amino acid. The results are presented in colony-forming units (CFU) per mg of RNA used for transfection. The ranges indicate variations between the experiments. FIG. 3C compares growth of the cells transfected with VEE replicons expressing GFP, and different capsids. The data were normalized on the number of viable adherent cells determined at 6 h post transfection. FIG. 3D shows analysis of cellular transcription. RNA labeling was performed with [$^3$H]uridine at 24 h post transfection for 2 h and RNA samples were analyzed by gel electrophoresis. Quantitative analysis of residual cellular transcription was performed as described in FIG. 1. Error bars indicate variations between parallel samples.

FIG. 4A is a schematic representation of VEEV genome-based replicons expressing $C_{VEE}$ and $C_{VEE}$GFP fusion. Analysis of the replicons' ability to establish persistent replication and develop Pur$^R$ foci. Arrows indicate the positions of the subgenomic promoters. FIG. 4B shows growth of the cells transfected with VEE replicons expressing either GFP or $C_{VEE}$. The data were normalized on the number of viable adherent cells determined at 6 h post transfection. FIG. 4C shows analysis of cellular transcription. RNA labeling was performed with [$^3$H]uridine at 24 h post transfection for 2 h. RNA samples were analyzed by gel electrophoresis. Quantitative analysis of residual cellular transcription was performed as described in FIG. 1. Error bars indicate variations between parallel samples. FIG. 4D shows analysis of the GFP-containing proteins expressed by indicated replicons. Cell lysates were prepared at 20 h post transfection and analyzed by western blotting using GFP-specific antibody.

FIG. 5A is a schematic representation of VEEV genome-based replicons expressing the deleted forms of capsid fused with GFP, and analysis of their ability to establish persistent replication and develop PurR foci. Arrows indicate the positions of the subgenomic promoters. Numbers indicate the first amino acid of CVEE after deletion. In all of the constructs, the initiating capsid AUG was present in its natural position. FIG. 5B compares growth of the cells carrying VEEV replicons expressing GFP or indicated fusions.

FIGS. 6A-6C compare effect of the expression of $C_{VEE}$ peptides fused with GFP or GFP$_{NLS}$ on cell viability and cellular transcription. FIG. 6A is a schematic representation of VEEV genome-based replicons expressing the deleted forms of capsid fused with GFP, and analysis of their ability to establish persistent replication and develop Pur$^R$ foci. Arrows indicate the positions of the subgenomic promoters. In all of the constructs, the initiating AUG was created upstream of the studied peptide. FIG. 6B shows growth of the cells carrying VEEV replicons expressing indicated fusions. FIG. 6C shows analysis of cellular transcription. RNA labeling was performed with [$^3$H]uridine at 24 h post transfection for 2 h. RNA samples were analyzed by gel electrophoresis. Quantitative analysis of residual cellular transcription was performed as described in FIG. 1. Error bars indicate variations between parallel samples.

FIGS. 7A-7C compares effects of $C_{VEE}$30-68 and $C_{EEE}$33-71 peptides, fused with GFP$_{NLS}$, on cellular transcription and cell viability. FIG. 7A is a schematic representation of VEEV genome-based replicons expressing GFP or fusion proteins.

The initiating AUG was created upstream of the studied peptides. Analysis of the replicons' ability to establish persistent replication and develop Pur$^R$ foci. FIG. 7B shows growth of the cells transfected with VEE replicons expressing indicated proteins. The data were normalized on the number of viable adherent cells determined at 6 h post transfection. FIG. 7C shows analysis of cellular transcription. RNA labeling was performed with [$^3$H]uridine at 24 h post transfection for 2 h. RNA samples were analyzed by gel electrophoresis. Quantitative analysis of residual cellular transcription was performed as described in FIG. 1. Error bars indicate variations between parallel samples.

In FIG. 8A, BHK-21 cells were transfected with the replicons expressing $C_{VEE}$GFP (a), $C_{VEE}$D35-47GFP (b) and $C_{VEE}$frshGFP (c) proteins, and the intracellular distribution of the fusions was analyzed at 12 h post transfection. The high magnification images of the nuclei-containing cell fragments were acquired on the confocal microscope. In FIG. 8B, BHK-21 cells were transfected with VEErepL/$C_{VEE}$GFP/Pac, and, at 12 h post transfection, cells were permeablized with 0.5% Triton X-100, stained with MAb414 antibodies and AlexaFluor 546-labeled secondary antibodies and analyzed on a confocal microscope. FIG. 8B: (a) Distribution of $C_{VEE}$/GFP on the nuclear membrane, (b) MAb414 staining of the same cell and (c) overlay of the images (fragment of the image indicated on panels a and b is shown).

FIGS. 9A-9C show replication of the VEEV TC-83 having mutated capsid protein. FIG. 9A is a schematic representation of the viral genomes. In VEEV/CSIN1, the natural N-terminal fragment, located upstream of the protease domain (aa 1-110), was replaced by its SINV-specific counterpart (aa 1-98), indicated by black box. In VEEV/Cfrsh, the capsid contained a frame-shift mutations that changed the peptide between aa 57 and 86. In FIG. 9B, BHK-21 cells were electroporated with 5 mg of in vitro-synthesized RNAs. One-fifth of the samples were seeded into 35-mm culture dishes. At the indicated times post infection, media were replaced by fresh media, and virus titers in the culture fluids were determined by a plaque assay on BHK-21 cells. Note that cells transfected with VEEV/CSIN1 and VEEV/Cfrsh RNAs continued to release virus after 24 h post transfection, when VEEV TC-83 RNA transfected cells developed a profound CPE. FIG. 9C shows survival of mice infected with indicated viruses. Six-day-old NIH Swiss mice were inoculated i.c. with indicated doses of viruses. Animals were monitored for two months. No deaths occurred after day 9 post infection in any of these experiments.

(FIG. 11A) BHK-21 cells were co-infected with packaged VEErep14xTomato-3xNLS and VEErep/$C_{VEE}$/GFP. (a) Distribution of 4xTomato-3xNLS protein; (b) distribution of GFP; (c) overlay of two images. (FIG. 11B) BHK-21 cells were co-infected with VEErep/4xTomato-M9 and VEErep/$C_{VEE}$/GFP replicons. (a) Distribution of 4xTomato-M9 protein; (b) distribution of GFP; (c) overlay of two images. (FIG. 11C) BHK-21 cells were co-infected with VEErep/4xTomato-H2b and VEErep/$C_{VEE}$/GFP replicons. (a) Distribution of 4xTomato-H2b protein; (b) distribution of GFP; (c) overlay of two images. (FIG. 11D) Distribution of fluorescent proteins in BHK-21 cells infected with either VEErep/$C_{VEE}$/GFP, or VEErep/4xTomato-M9, or VEErep/4xTomato-H2b. Cells infected with VEErep/4xTomato-3xNLS are presented in FIG. 10. All of the images were acquired at 8 h post infection. Bars correspond to 20 mm. The schematic representation of the replicons is shown on each panel.

(FIG. 13A) BHK-21 cells were co-infected with packaged VEErep/4xTomato-3xNLS and VEErep/$C_{SIN}$/GFP. (a) Distribution of 4xTomato-3xNLS protein; (b) distribution of GFP; (c) overlay of two images. (FIG. 13B) BHK-21 cells were co-infected with VEErep/4xTomato-3xNLS and VEErep/$C_{VEE}$1-68-GFP replicons. (a) Distribution of 4xTomato-3xNLS protein; (b) distribution of $C_{VEE}$1-68-GFP; (c) overlay of two images. (FIG. 13C) BHK-21 cells were co-infected with VEErep/4xTomato-3xNLS and VEErep/$C_{VEE}$frsh-GFP replicons. (a) Distribution of 4xTomato-3xNLS protein; (b) distribution of $C_{VEE}$frsh-GFP; (c) overlay of two images. (FIG. 13D) BHK-21 cells were co-infected with VEErep/4xTomato-3xNLS and VEErep/$C_{VEE}$-GFP replicons. (a) Distribution of 4xTomato-3xNLS protein; (b) distribution of $C_{VEE}$-GFP; (c) overlay of two images. All of the images were acquired at 8 h post infection. Bars correspond to 20 mm. The schematic representation of the replicons is shown on each panel.

(FIG. 14A) nsP2 distribution in BHK-21 cells, (FIG. 14B) in NIH 3T3 cells and (FIG. 14C) in HEK293 cells. Staining was performed at 8 h post infection. (FIG. 14D) Staining of the mock-infected cells with VEEV nsP2-specific antibodies. Panels (a) staining with VEEV nsP2-specific antibodies, (b) nuclear staining with SYTOX Orange, (c) overlays of the images. All of the images were acquired at 8 h post infection. Bars correspond to 20 mm. The schematic representation of the replicons is shown on each panel.

(FIG. 15A) Intracellular distribution of SINV nsP2 during SINV Toto 1101 replication or (FIG. 15B) replication of SINNEEV recombinant virus in BHK-21 cells. (FIG. 15C) Staining of the mock-infected BHK-21 cells. Panels (a) staining with the SINV nsP2-specific antibodies, (b) nuclear staining with SYTOX Orange, (c) overlays of the images. Staining was performed at 8 h post infection. Images were acquired at 8 h post infection. Bars correspond to 20 mm. The schematic representation of the replicons is shown on each panel. In the schematic representations of viral genomes, SINV-specific sequences are indicated by open boxes, VEEV sequences are indicated by filled boxes.

(FIG. 17A) Distribution of VEEV nsP2 in the cells infected with VEErep/Cherry. (a) Staining with VEEV nsP2-specific antibodies; (b) distribution of Cherry; (c) overlay of two images. (FIG. 17B) Distribution of VEEV nsP2-HA in the cells, infected with SINrep2V/nsP2VEE-HA replicon. (a) Staining with anti-HA antibodies; (b) nuclear staining with SYTOX Orange; (c) overlay of two images. All of the images were acquired at 8 h post infection. Bars correspond to 20 mm. The schematic representation of the replicons is shown on each panel.

DETAILED DESCRIPTION OF THE INVENTION

Figure 1C:
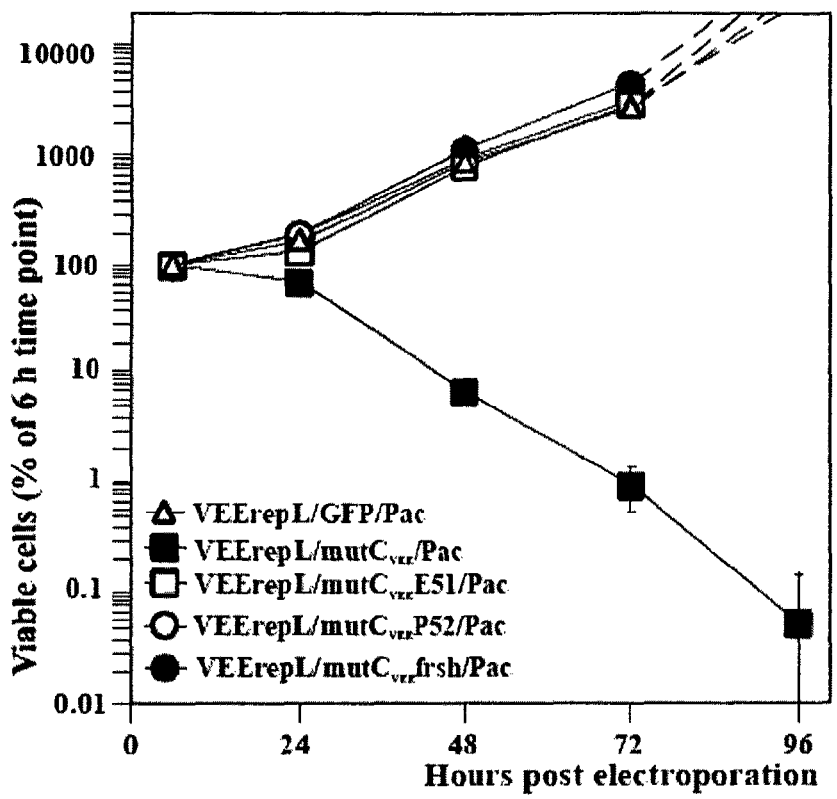

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, "active immunization" is defined as the administration of a immunogenic composition to stimulate the host immune system to develop immunity against a specific pathogen or toxin.

The immunogenic composition may comprise an adjuvant. As used herein, "adjuvant" is defined as a substance which when included in an immunogenic formulation non-specifically enhances the immune response to an antigen.

The natural transmission cycle of the VEEV and other alphaviruses implies their persistent replication in mosquito vectors and development of high-titer viremia in vertebrate hosts that is required for infection of new mosquitoes during the blood meal. The level of viremia and its duration are the critical factors that determine the successful continuation of the enzootic cycle and virus persistence in nature. However, like any other viral infection, alphavirus replication in vertebrate cells induces a response aimed at downregulation of virus production and activation of cell signaling, leading to activation of the antiviral state in the uninfected cells and prevention of successive rounds of infection. As did most, if not all of other viruses, alphaviruses developed efficient mechanisms of interference with the cellular response, and one of them is based on the inhibition of cellular transcription (9, 13).

In the Old World alphaviruses SINV and SFV, the nonstructural protein nsP2 is a key factor in the inhibition of transcription of cellular messenger and ribosomal RNAs. However, the New World alphaviruses VEEV and EEEV employ not the nsP2, but the structural, capsid protein, for achieving the same goal. Capsid protein is efficiently expressed in the infected cells and distributed both in the cytoplasm and in the nuclei. Besides packaging of viral genome RNA, VEEV- and EEEV-specific capsids are transported into nuclei and cause global inhibition of cellular transcription that strongly correlates with cytopathic effect development. The results of this study demonstrate that both cytopathic effect development and transcription inhibition are determined by the same, short, N-terminal peptide of $C_{VEE}$, positioned between amino acid 33 and 69. It is difficult to expect that such a short peptide has two separate functions: transcriptional shutoff and cytopathic effect induction. Most likely, cytopathic effect develops is a result of transcriptional block. However, a possibility that both phenomena can be determined by different mechanisms cannot be completely ruled out.

The identified functional peptide can be provisionally divided into two domains: i) a previously defined a-helix, HI, (amino acids 34-51) (31, 32) that is present in all of the alphavirus capsids and has been shown to function in core assembly, and ii) a downstream, highly positively charged peptide located between amino acid 51 and 69. The amino acid sequences of both domains demonstrate a strong conservation among the New World alphaviruses, but these peptides differ from the sequences in the Old World alphavirus capsid, which are nonfunctional in transcription inhibition and incapable of causing CPE. Alterations of each domain in $C_{VEE}$34-68 have strong negative effects on the ability of the entire $C_{VEE}$ or minimal $C_{VEE}$30-68 peptide to cause transcriptional shutoff and CPE development. However, these mutations appear to affect different functions. $C_{VEE}$GFP fusion lacking the HI domain ($C_{VEE}$D35-47GFP) accumulated only in the cell nuclei, and $C_{VEE}$frsh having a frame-shift mutation in the downstream peptide (aa 58-85) was no longer transported to the nucleus. The latter frame-shift mutation changed an amino acid 58-85 sequence in a very interesting way: the peptide remained highly hydrophilic and became even more positively charged. However, based on the computer prediction, the putative NLSs, located between amino acids 64 and 85, were destroyed. $C_{VEE}$GFP fusion protein is larger than the proteins that can passively diffuse to the nucleus, but a significant fraction of this protein was found in that compartment. Since the frame-shift mutation made fusion protein incapable of translocation to the nuclei, this finding was a strong indication that the NLSs predicted after amino acid 64 are indeed functional and drive the $C_{VEEGFP}$ and, most likely, $C_{VEE}$ itself into the nucleus.

The increase in nuclear localization of $C_{VEE}$ after HI deletion might be explained in different ways. First, as described for $C_{SIN}$ (31, 32), the HI deletion might strongly affect the nucleocapsid assembly and, consequently, the balance between the core-associated capsid cores and the free form of this protein that, as indicated above is capable of translocation to the nucleus. Another explanation is that in addition to the proposed another peptide (50), functioning in $C_{SIN}$ binding to the ribosomes, VEEV HI is involved in this function and, thus in retaining of $C_{VEE}$ in the cytoplasm. Finally, $C_{VEE}$-HI might function as a nuclear export signal, and the balance between $C_{VEE}$ import to the nucleus and its export determines its intracellular distribution.

The most important result was, however, not in the changes of $C_{VEE}$ compartmentalization due to HI deletion or mutations in amino acids 58-85 peptide, but in the detected inability of the mutated proteins to inhibit cellular transcription and cause cytopathic effect. The accumulation of HI deletion mutant in the nucleus did not noticeably affect cell biology and strongly suggested that HI functions not only in the core assembly and control of intracellular distribution of capsid; this sequence appears to be also strongly involved in the development of transcriptional shutoff. Similar conclusions can be made about the $C_{VEE}$52-68 domain: it certainly contains a functional NLS, but the point mutations in 51 and 52 (outside the NLS) also made $C_{VEE}$ incapable of inhibiting transcription. Moreover, the addition of the artificial NLS to $C_{VEE}$30-60GFP fusion (having the natural NLS deleted) did not restore the ability of this protein to inhibit cellular transcription, indicating that 52-68 peptide activities are likely more extensive than just acting as an NLS. Thus, both domains, the HI and amino acids 52-68, appear to have more sophisticated functions in regulation of cellular transcription than control of capsid distribution alone.

One of the possible explanations for this new capsid activity may lie in the modification of nucleocytoplasmic transport. Significant fractions of $C_{VEE}$GFP (FIGS. 8A-8B) and $C_{VEE}$30-68GFP were detected on the nuclear membrane, where they demonstrated a distribution similar to that of the NPCs, suggesting interaction of Nups and $C_{VEE}$. To date, inhibition of nuclear transport has been described only for a very limited number of viruses, among which VSV, poliovirus, rhinovirus and cardiovirus are better studied (16, 28, 33, 37). The VSV matrix protein interacts with the nucleoporin Nup98 and export receptor Rae 1 (8). Thus, M protein accumulates in the NPC (34), in which it efficiently inhibits Rae 1-mediated mRNA nuclear export (34, 46) and slows the rate of the nuclear import through importin a/b1-dependent pathway (33). Interestingly, VSV also efficiently inhibits cellular transcription (4), but the correlation between inhibition of nucleocytoplasmic traffic and downregulation of transcription has not been investigated. Picornaviruses have been shown to alter nucleocytoplasmic transport either by the protease-dependent processing of nucleoporins (17, 18) or by disruption of the RanGDP/GTP gradient (37). Therefore, VEEV and, most likely, other New World aphaviruses appear to join a growing number of pathogens that interfere with the activation of cellular genes that function in the antiviral response, by modifying nucleocytoplasmic transport.

The importance of $C_{VEE}$ localization on the NPC is currently supported by two findings: i) a significant fraction of $C_{SIN}$ (the noncytopathic capsid) is present in the nucleus, but is not associated with the nuclear membrane, and this might be a plausible explanation of $C_{SIN}$'s inability to cause transcriptional shutoff. ii) As indicated above, $C_{VEE}$ with a deleted HI sequence is present in the nucleus in a high concentration; however, it does not accumulate on the nuclear membrane/nuclear pores, and this strongly correlates with $C_{VEE}$D36-47 (having HI deleted) inability to inhibit transcription. Moreover, it was observed that $C_{VEE}$ inhibits at least one nuclear import pathway that is mediated by the importin-a/b receptors, and prevents translocation of the SV40 NLS-containing proteins to the nuclei.

The importance of newly identified functions of $C_{VEE}$ for virus replication was strongly supported by in vitro and in vivo experiments with replicating VEEV TC-83, encoding modified versions of capsid. The replacement of the entire N-terminal fragment of $C_{VEE}$ with that of $C_{SIN}$ in VEEV/$C_{sin1}$ did not noticeably change replication of the virus in BHK-21 cells, and the original VEEV TC-83 and VEEV/$C_{sin1}$ demonstrated nearly identical growth rates. However, the mutated virus was dramatically less cytopathic and cells continued to release infectious virus days after complete cytopathic effect development in VEEV TC-83-infected samples. Moreover, this mutant was more attenuated in vivo than the currently available vaccine strain TC-83. The introduction of the above-described frame-shift mutations into the capsid gene of TC-83 had a detectable negative effect on virus replication. This lower level of virus replication might explain its more attenuated phenotype in vivo. However, its strongly altered ability to cause cytopathic effect in cultured cells points to the possibility that a change in $C_{VEE}$ interactions with cellular transcriptional machinery may also be involved.

Taken together, the present invention suggests new ways of New World alphavirus attenuation: i) the identified critical domain of VEEV, EEEV and WEEV capsid proteins can be modified by point mutations or small deletions, or ii) the large fragments of the protein can be replaced by the Old World alphavirus-derived counterparts. The second direction may prove more promising, because one of the distinguishing features of alphaviruses is in their extraordinarily high mutation rates and adaptation. Therefore, the effect of point mutations and small deletions, which have a negative effect on virus growth rates are usually neutralized by adaptive, compensatory mutations within a few subsequent passages in vivo or in vitro. It will be, likely, more difficult to adapt the entire N-terminal, SINV-specific fragment (C1-98) or the entire $C_{SIN}$, which did not become capable of inducing transcriptional shutoff during the entire, previous virus evolution.

In conclusion, the present invention developed attenuated alphavirus that can be used as vaccines having irreversible, attenuated phenotype. In general, representative alphaviruses of the present invention have modified capsid proteins and are capable of efficient replication in tissue culture but cannot cause disease in the animals and immunized individuals. Specifically, the present invention demonstrates that (i) the N-terminal fragments of VEEV, EEEV and, most likely, of WEEV capsid proteins contain a ~35-α-long peptide that functions in the inhibition of cellular transcription and cytopathic effect development; (ii) the identified, VEEV-specific peptide, $C_{VEE}$30-68, includes two domains with distinguished functions: the a-helix domain, HI, that is critically involved in supporting the balance between the presence of the protein in the cytoplasm and nucleus, and the C-terminal peptide that contains the NLS(s). The integrity of both domains determines the intracellular distribution of $C_{VEE}$, and both are essential for capsid function in the inhibition of transcription; (iii) $C_{VEE}$ appears to interact with NPC, and this interaction correlates with the protein's ability to cause transcriptional shutoff, and, ultimately, cytopathic effect development; and (iv) the replacement of the N-terminal fragment of $C_{VEE}$ by its SINV-specific counterpart in VEEV TC-83 genome does not affect virus replication in vitro, but makes it strongly less cytopathic and more attenuated in vivo.

The present invention is directed to a method of attenuating New World encephalitogenic alphavirus comprising: mutating one or more than one amino acids in the amino terminal of the capsid protein of the alphavirus; or replacing the entire capsid protein or amino terminal of the capsid protein of the alphavirus by capsid protein or amino terminal of less pathogenic Old World alphavirus. Examples of the mutation is not limited to but may include a point mutation of the amino acids in the amino terminal of the capsid protein. The amino acid(s) mutated or replaced is not limited to but may include amino acids 33-68 of Venezuelan Equine Encephalitis virus capsid protein, amino acids 36-72 of Eastern Equine Encephalitis virus capsid protein or amino acids 36-72 of Western Equine Encephalitis virus capsid protein. Furthermore, the Old World alphavirus may include but is not limited to Sindbis, Semliki Forest, Ross River, Aura and other antigenically related viruses. Additionally, the attenuated New World, encephalitogenic alphavirus may be capable of replicating in vitro but cannot cause disease in animals and in immunized individuals.

The present invention is also directed to an immunogenic composition, comprising the attenuated New World encephalitogenic alphavirus generated by the method described supra. Such attenuated New World encephalitogenic alphavirus may comprise mutations of one or more than one amino acids in the amino terminal of the capsid protein of the alphavirus, deletion of entire capsid protein or deletion of amino terminal of the capsid protein. The deleted capsid protein or amino terminal of the capsid protein may be replaced by capsid protein or amino terminal of the capsid protein of less pathogenic Old World alphavirus. Examples of the amino acid(s) mutated or replaced may include but is not limited to amino acids 33-68 of Venezuelan Equine Encephalitis virus capsid protein, amino acids 36-72 of Eastern Equine Encephalitis virus capsid protein or amino acids 36-72 of Western Equine Encephalitis virus capsid protein. Examples of the Old World alphavirus may include but is not limited to Sindbis, Semliki Forest, Ross River, Aura and other antigenically related viruses.

The present invention is also directed to a method of preventing an infection caused by Old and New World encephalitogenic alphavirus in a subject, comprising: administering an immunologically effective amount of the immunogenic composition described supra to the subject. Examples of the New World encephalitogenic alphavirus may include but is not limited to Venezuelan Equine Encephalitis virus, Western Equine Encephalitis virus or Western Equine Encephalitis virus and those of the Old World alphavirus may include but is not limited to Sindbis virus, Semliki Forest virus, Ross River virus or Aura virus. Such an immunogenic composition may be administered subcutaneously or intramuscularly. Additionally, the subject may be a human or an animal, where the subject may be a healthy subject or a subject who is likely to be exposed to the alphavirus.

Treatment methods will involve preventing an infection in a subject with an immunologically effective amount of a composition described supra. An immunologically effective amount is described, generally, as that amount sufficient to detectably and repeatedly induce an immune response so as to prevent, ameliorate, reduce, minimize or limit the extent of a disease or its symptoms. More specifically, it is envisioned that the treatment with the immunogenic composition elicits an antibody response and/or decreases the viral load in the subject to prevent the infection caused by the New World and Old World encephalitogenic alphavirus.

The immunologically effective amount of the immunogenic composition to be used are those amounts effective to produce beneficial results, particularly with respect to preventing the infection caused by the New World and Old World encephalitogenic alphavirus, in the recipient animal or human. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

The immunogenic composition disclosed herein may be administered either alone or in combination with another drug or a compound. Such a drug or compound may be administered concurrently or sequentially with the immunogenic composition disclosed herein. The effect of co-administration with the immunogenic composition is to lower the dosage of the drug or the compound normally required that is known to have at least a minimal pharmacological or therapeutic effect against the disease that is being treated. Concomitantly, toxicity of the drug or the compound to normal cells, tissues and organs is reduced without reducing, ameliorating, eliminating or otherwise interfering with any cytotoxic, cytostatic, apoptotic or other killing or inhibitory therapeutic effect of the drug or the compound.

The composition described herein and the drug or the compound may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The immunogenic composition described herein and the drug or the compound may be administered independently one or more times to achieve, maintain or improve upon a therapeutic effect. It is well within the skill of an artisan to determine dosage or whether a suitable dosage of either or both of the immunogenic composition and the drug or the compound comprises a single administered dose or multiple administered doses.

As is well known in the art, a specific dose level of such an immunogenic composition generated thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the immunologically effective amount of the immunogenic composition generated thereof can be the amount that is required to achieve the desired result: enhance antibody response, decrease the bacterial load, etc.

Administration of the immunogenic composition of the present invention to a patient or subject will follow general protocols for the administration of therapies used in treatment of infections taking into account the toxicity, if any, of the components in the immunogenic composition, the antibody and/or, in embodiments of combination therapy, the toxicity of the antibiotic. It is expected that the treatment cycles would be repeated as necessary. It is also contemplated that various standard therapies, as well as surgical intervention, may be applied in combination with the described therapy.

As is known to one of skill in the art the immunogenic composition described herein may be administered along with any of the known pharmacologically acceptable carriers. Additionally the immunogenic composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cell Cultures

BHK-21 cells were provided by Dr. Sondra Schlesinger (Washington University, St. Louis, Mo.). NIH 3T3 cells were obtained from the American Type Culture Collection (ATCC) (Manassas, Va.). Both cell lines were maintained at 37° C. in alpha minimum essential medium (aMEM) supplemented with 10% fetal bovine serum (FBS) and vitamins.

EXAMPLE 2

Plasmid Constructs

VEErepL replicon, having a mutation in the nsP2 gene, Q739→L, is described elsewhere (12, 35). The distinguishing feature of this replicon is in its noncytopathic phenotype and low level of genome RNA replication and transcription of the subgenomic RNA. Such replicons do not overproduce the proteins of interest and generate biologically relevant data. VEErepL/GFP/Pac replicon, used as a noncytopathic control in many experiments, is described elsewhere (11). The genes of tested proteins were cloned into VEErepL under the control of the subgenomic promoter, and the second promoter was driving the expression of puromycin acetyl transferase (Pac) that makes the replicon-containing cells resistant to translational arrest caused by puromycin. All of the tested cassettes expressing capsid protein with different deletions were synthesized by PCR and sequenced before cloning into the vector replicon as GFP fusions. The selection of frameshift mutant of CVEE is described elsewhere (12), and the corresponding gene was synthesized by RT-PCR using the RNA, isolated from the growing, replicon-containing cells. The capsid-specific peptides were separated from GFP by short, flexible peptide 4xGly. All of the GFP fusions were designed in a way to avoid cleavage by the capsid-encoded protease. To achieve this, the last amino acid in capsid was deleted. An additional AUG codon was added to all of cassettes encoding VEEV- and EEEV-specific peptides that did not contain the initiating AUG. VEEV/CSIN1 encoded the infectious VEEV TC-83 genome, in which the sequence encoding amino acid 1-110 of CVEE was replaced by sequence encoding aa 1-1-98 of CSINV. VEEV/CVEEfrsh genome encoded capsid, having previously identified frame shift mutations (12).

EXAMPLE 3

RNA Transcriptions

Plasmids were purified by centrifugation in CsCl gradients. Before being subjected to a transcription reaction, plasmids were linearized using the MluI or NotI restriction sites located downstream of the poly(A) sequence of VEE replicons. RNAs were synthesized by SP6 RNA polymerase in the presence of a cap analog by described conditions (38). The yield and integrity of transcripts were analyzed by gel electrophoresis under non-denaturing conditions. RNA concentration was measured on a Fluor Chem imager (Alpha Innotech), and transcription reactions were used for electroporation without additional purification.

EXAMPLE 4

Analysis of Cytotoxicity of the Constructs

BHK-21 cells were electroporated as described (29). In all of the experiments, 5 mg of the in vitro-synthesized RNAs was used per electroporation of $5 \times 10^6$ cells. Next, the aliquots of the cells were seeded into 6-well Costar plates for analysis of cell proliferation and viability as described elsewhere (11, 12). Puromycin selection (10 mg/ml) was performed between 6 and 48 h post transfection. Then cells were incubated in puromycin-free media, and viable cells were counted at the times indicated in the figures. In parallel, different dilutions of the electroporated cells were seeded into 100-mm tissue culture dishes. At 6 h post transfection, puromycin was added to the media to a concentration of 10 mg/ml. Colonies of $Pur^R$ cells were stained with crystal violet at days 4-9 post transfection, depending on their growth rates. The results are expressed in colony-forming units (CFU) per mg of RNA used for transfection.

EXAMPLE 5

Analysis of Cellular Transcription

BHK-21 cells were electroporated by 5 mg of the in vitro-synthesized RNAs and one-tenth of the cells were seeded into 35-mm culture dishes. At 6 h post transfection, puromycin was added to the media to a concentration of 10 mg/ml. At indicated times post electroporation, the cellular RNAs were labeled for the time periods given in figure legends in the complete aMEM supplemented with 10% FBS and 20 mCi/ml [$^3$H]uridine without addition of ActD. The RNAs were isolated by TRizol reagent as recommended by the manufacturer (Invitrogen) and analyzed by agarose gel electrophoresis as previously described (5).

To assess the total RNA synthesis, the RNA samples on the Whatman 3mM paper were washed with cold 10% Trichloroacetic acid (TCA), and radioactivity was measured by liquid scintillation counting and normalized on the number of viable cells determined by the above described tests.

EXAMPLE 6

Infectious Center Assay

Five mg of in vitro-synthesized, full-length RNA transcripts of viral genomes was used per electroporation. Tenfold dilutions of electroporated BHK-21 cells were seeded in six-well Costar plates containing subconfluent naïve cells. After 1 h incubation at 37° C. in a 5% $CO_2$ incubator, cells were overlaid with 2 ml of MEM-containing 0.5% Ultra-Pure agarose supplemented with 3% FBS. Plaques were stained with crystal violet after 2 days incubation at 37° C.

EXAMPLE 7

Viral Replication Analysis

To exclude any effect of possible virus evolution on the replication efficiency, virus growth rates were evaluated directly after electroporation of the in vitro-synthesized RNA into the cells. BHK-21 cells were electroporated by 5 mg of the RNAs, and one-fifth of the cells were seeded into 35-mm culture dishes. At the indicated times post infection, media were replaced by fresh media, and virus titers in the culture fluids were determined by a plaque assay on BHK-21 cells as previously described (26).

EXAMPLE 8

Immunization and Challenge with Virulent VEEV

Weanling, female, six-day-old mice were inoculated i.c. with VEE TC-83 or other designed viruses at a dose of $10^7$ plaque-forming units in a total volume of 20 µl of PBS. After vaccination, each cohort of 10 animals was maintained for 21 days without any manipulation. Mice were observed twice daily for clinical illness (noting those with ruffled coat, depression, anorexia and/or paralysis) and/or death.

EXAMPLE 9

Microscopy

BHK-21 cells were seeded on glass chamber slides (Nunc) and transfected with 2 mg of in vitro-synthesized replicon RNA using Lipofectamine 2000 according to the manufacturer's instructions (Invitrogen). Then, at 12 h post transfection, they were fixed in 3% formaldehyde in phosphate buffered saline (PBS), and the distribution of the GFP-containing fusion proteins was analyzed on a Zeiss LSM510 META confocal microscope using a 63×1.4NA oil immersion planapochromal lens. For staining of nucleopore complexes (NPC), cells were additionally permeablized with 0.5% Triton X-100, stained with MAb414 antibodies (Covance Innovative Antibodies) and AlexaFluor 546-labeled secondary antibodies and analyzed using a confocal microscope.

EXAMPLE 10

The Mutations in VEEV Capsid Protein Affect its Ability to Cause both CPE and Transcription Inhibition VEEV capsid was expressed from VEEV replicons having a mutation in nsP2 that decreased RNA replication as described (12). Capsid production caused rapid CPE development and inhibited RNA polymerase I- and II-dependent cellular transcription. However, fewer than 0.1% of the cells continued to grow, and their ability for growth correlated with an accumulation of mutations in the replicon-encoded capsid gene. The majority of mutations destroyed the ORF downstream of the amino acid 50 of the capsid-coding sequence, but others changed either a single amino acid: $K_{51} \rightarrow E$ or $Q_{52} \rightarrow P$, or a short peptide between amino acid 57 and 86 (58-85-frame shift). However, the latter point and frame-shift mutations were detected only in the capsid gene (mutC$_{VEE}$) that encoded the protein with inactive protease ($S_{226} \rightarrow A$ mutant). Therefore, it was not clear whether the $K_{51} \rightarrow E$, $Q_{52} \rightarrow P$ and frame shift mutations strongly affected the ability of the protein to cause CPE, or if this was a synergistic effect of these mutations and inactivation of protease activity by the $S_{226} \rightarrow A$ replacement.

Figure 1D:
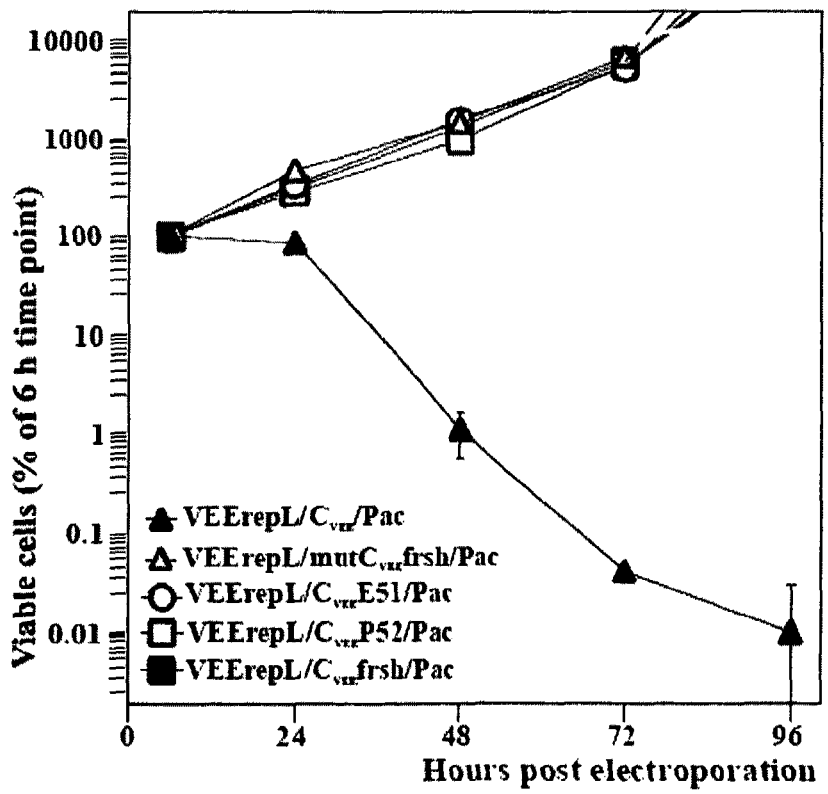
Figure 1E:
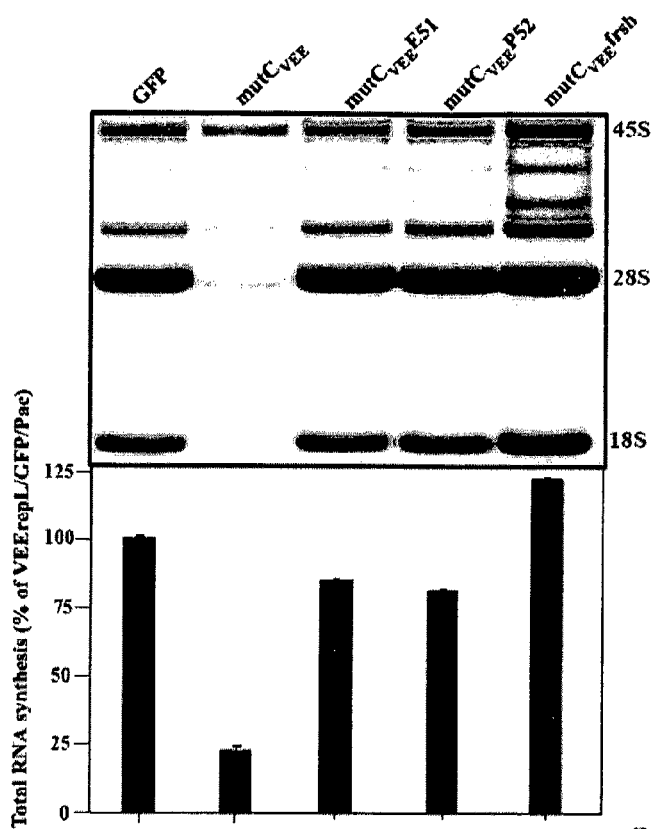
Figure 1F:
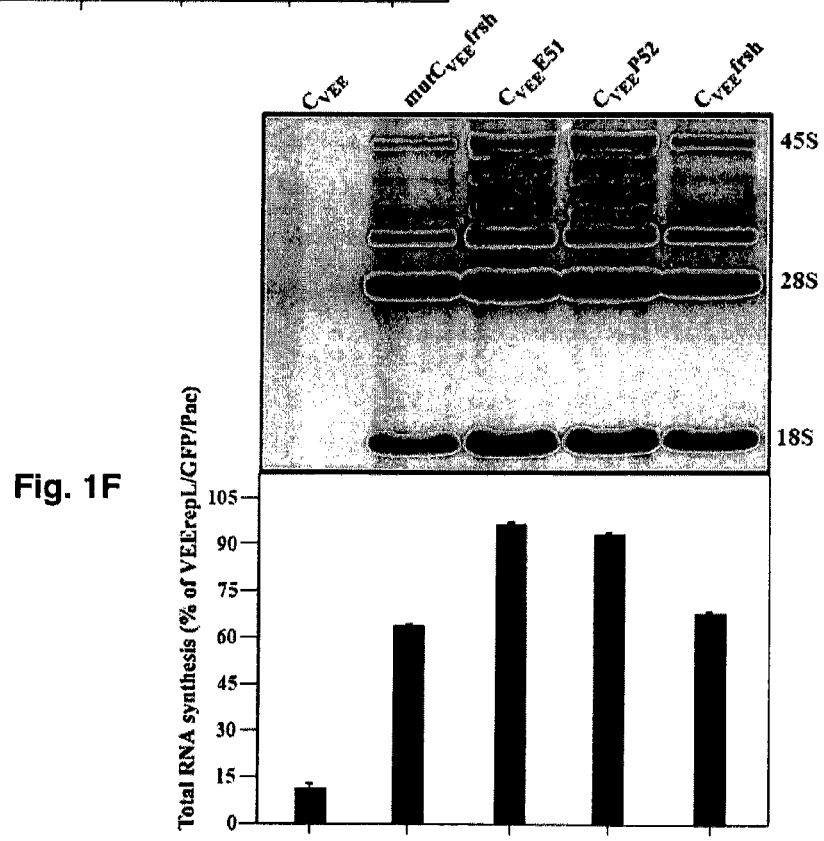

To distinguish between these two possibilities and to further evaluate the effect of the mutations on $C_{VEE}$ function, the above described $K_{51} \rightarrow E$, $Q_{52} \rightarrow P$ and frame-shift mutations were cloned into VEErepL/mutC$_{VEE}$/Pac replicon, in which capsid gene encoded a protease mutant, and into similar replicon that encoded a wt capsid, VEErepL/C$_{VEE}$/Pac (FIGS. 1A-1B). All of the replicons were synthesized in vitro, and equal amounts of RNAs were transfected into BHK-21 cells. Replicons encoding GFP and capsids without the indicated mutations were used as controls. The cytopathicity of the expressed capsids was examined by evaluating the number of Pur$^R$ foci formed per mg of transfected RNA (FIGS. 1A-1B) and measuring the growth of the Pur$^R$ cells (FIGS. 1C-1D). Additionally, the ability of the expressed proteins to inhibit cellular transcription was also assessed (FIGS. 1E-1F).

All of the mutations previously identified in the mutC$_{VEE}$ gene ($K_{51} \rightarrow E$, $Q_{52} \rightarrow P$ and 58-85-frame shift) made the capsid and designed replicons noncytopathic, regardless of their presence in $C_{VEE}$ or mutC$_{VEE}$. These mutations also made capsids incapable of inhibiting cellular transcription. In repeated experiments, cells containing replicons driving the expression of the indicated capsid mutants demonstrated the same growth rates as untransfected control or cells containing VEErepL/GFP/Pac. These data unambiguously demonstrated that $C_{VEE}$-encoded protease activity is not involved in CPE development and downregulation of cellular transcription, but these phenomena were, most likely, the function of the N-terminal capsid-specific peptide (amino acid 1-110) that was previously identified as a domain functioning in RNA packaging and nucleocapsid formation.

EXAMPLE 11

Deletion Analysis of the VEEV Capsid Protein

Alphavirus capsid protein was shown to contain two structural domains. The C-terminal domain expresses a protease activity required for co-translational self-cleavage of capsid from the structural polyprotein (19, 20). The N-terminal domain is highly positively charged (39) and functions in packaging of the viral genome during core assembly (42). This domain is known to be unfolded (7), except for a short peptide that is predicted to form an alpha helix (HI) and is present in the capsid of all alphaviruses (31, 32). This data indicated that the N-terminal, and not the C-terminal domain determines $C_{VEE}$ function in CPE development and inhibition of cellular transcription. Therefore, to identify a particular peptide that exhibits these inhibitory effects, a detailed deletion analysis was performed wherein N-terminal $C_{VEE}$ fragments were expressed as GFP fusions from the VEErepL replicon. The use of GFP-tagged fragments allowed following changes in the intracellular distribution of the protein and to some extent, mimic the natural structure of original $C_{VEE}$, because in this case, the folded, C-terminal domain was replaced by GFP that also demonstrates a globular structure. Such fusion proteins had molecular weights similar to that of the $C_{VEE}$.

To make the data consistent with the previous results, the fusions were expressed from the VEErepL replicon. Both the $C_{VEE}$110GFP fusion that expressed the entire N-terminal domain, and the $C_{VEE}$80GFP (FIG. 2A), having the highly positively charged fragment deleted, were highly efficient in causing both cell death (FIG. 2B) and inhibition of cellular transcription (FIG. 2C), and very few replicon-containing cells developed $Pur^R$ foci. These data indicated that the critical peptide was located upstream of the deletions made.

Figures 2C, 3A:
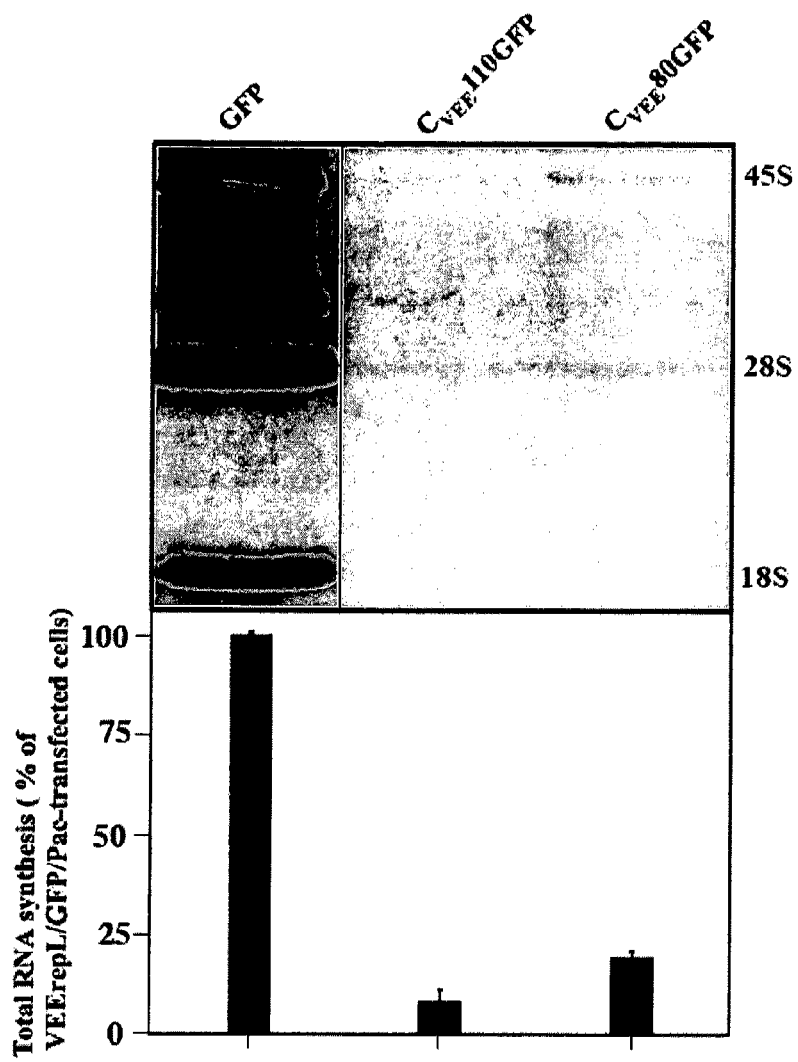
Figure 3D:
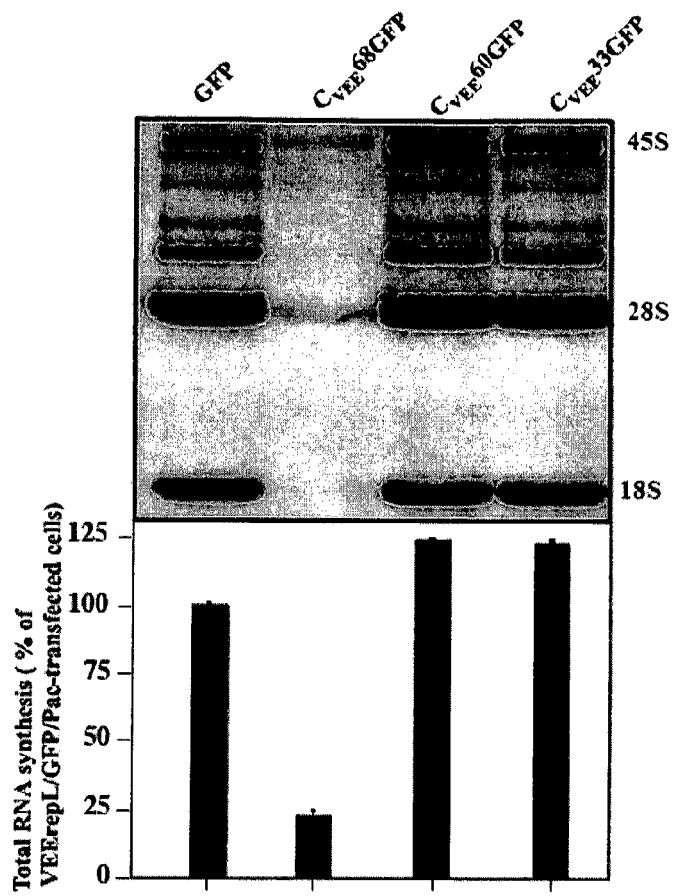

The next set of deletions was designed based on the alignment of the N-terminal $C_{VEE}$ fragment with that of other alphaviruses. The high number of amino acids in the 34-68 peptide of $C_{VEE}$ is identical to those in the corresponding fragments of other New World alphaviruses, EEEV and WEEV, but not in the Old World alphaviruses (whose capsids are not cytopathic) (FIG. 3A). This finding pointed to the possibility that these amino acids might determine the activity of the New World alphavirus capsids in transcription inhibition. Therefore, the sequence of the $C_{VEE68}$ peptide encoding the entire conserved peptide was fused with GFP and expressed it from VEErepL replicon (FIG. 3B). Other constructs had either partial deletion of this sequence ($C_{VEE}$60GFP) or the deletion of the entire conserved fragment downstream of the amino acid 33 ($C_{VEE}$33GFP). The results were in agreement with the assumption about the critical role of the amino acid 34-68 peptide in virus-host cell interactions: the expression of $C_{VEE}$68GFP fusion caused CPE (FIG. 3C) and, by 24 h post transfection, downregulated cellular transcription to an almost undetectable level (FIG. 3D). $C_{VEE}$60 and $C_{VEE}$34 were incapable of causing transcriptional shutoff, and GFP-tagged peptides were as noncytopathic as GFP itself. Taken together, these data indicated that a protein fragment located upstream of the amino acid 68 is critically involved in the inhibition of cellular transcription and cytopathic effect development.

Figure 4A:
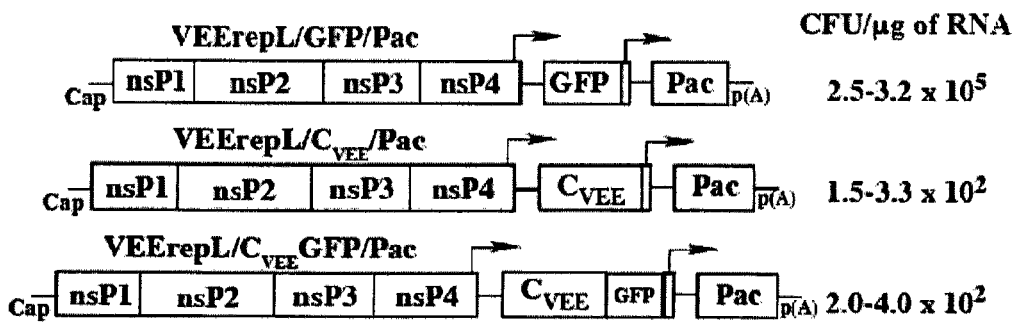
FIGS. 4A-4D show comparison of the effects of $C_{VEE}$ and $C_{VEE}$GFP fusions expression on cellular transcription and cell viability.
Figure 4D:
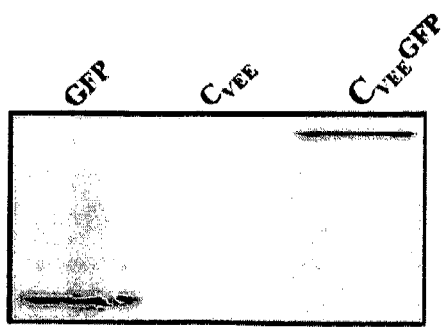
Figure 4B:
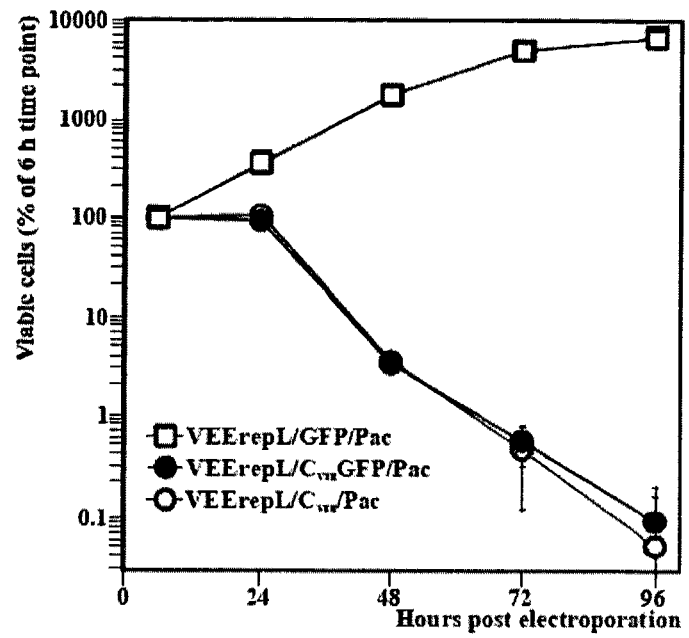
Figure 4C:
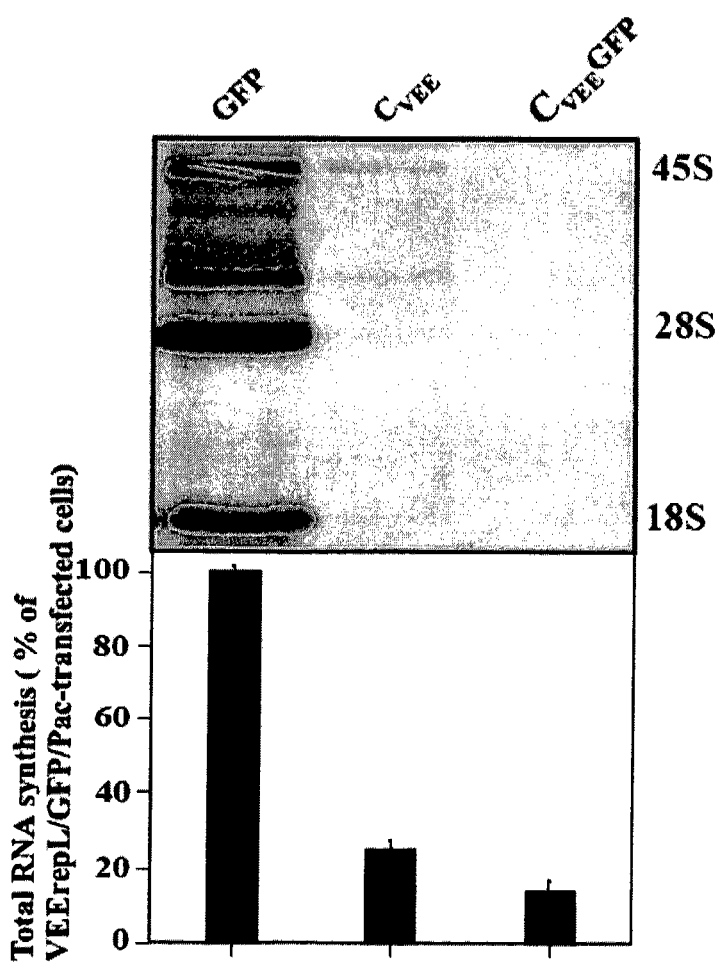

To define the beginning of the critical peptide, the $C_{VEE}$ deletion mutants were designed in the context of complete $C_{VEE}$GFP fusion. Therefore, initial experiments were aimed at demonstrating that such fusion has exactly the same functions in modification of cell biology as $C_{VEE}$ itself. The last amino acid in the capsid was deleted to avoid cleavage of the fusion by capsid-associated protease, and fusion with GFP was performed through a flexible peptide. The in vitro-synthesized VEErepL/$C_{VEE}$GFP/Pac and control replicons VEErepL/$C_{VEE}$/Pac and VEErepL/GFP/Pac (FIG. 4A) were transfected into BHK-21 cells. $C_{VEE}$GFP-expressing cells developed cytopathic effect at exactly the same rate as those expressing $C_{VEE}$ (FIG. 4B) and demonstrated the same inhibition of cellular transcription (FIG. 4C). The mutation introduced into the C-terminus abolished cleavage, and the detected phenotype could not be explained by partial processing (FIG. 4D).

Figure 5A:
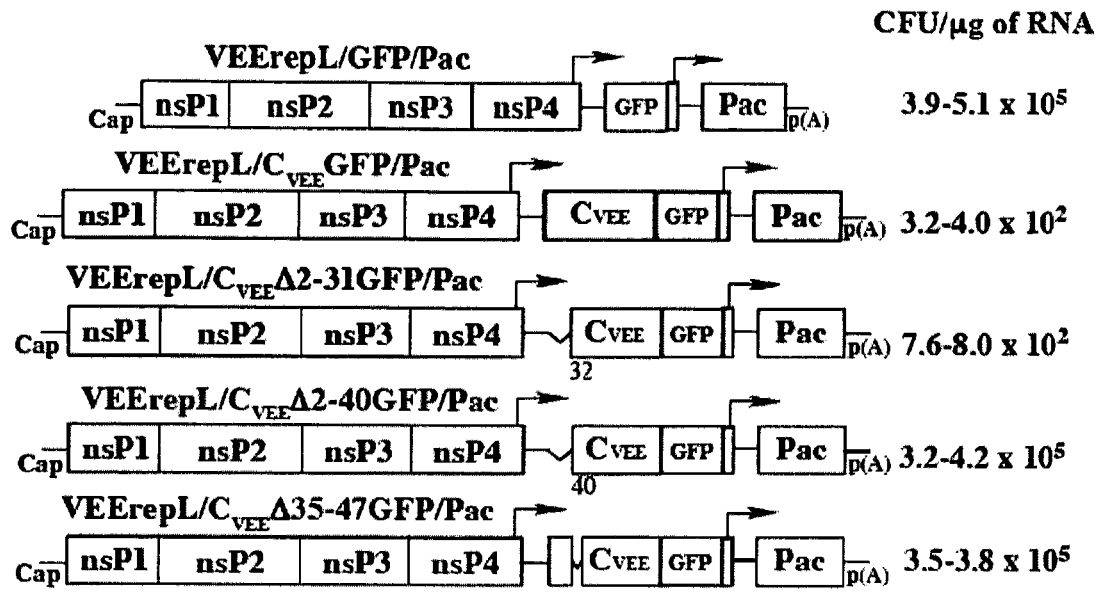
FIGS. 5A-5B show effect of the N-terminal deletions in capsid on cellular transcription and cell viability.
Figure 5B:
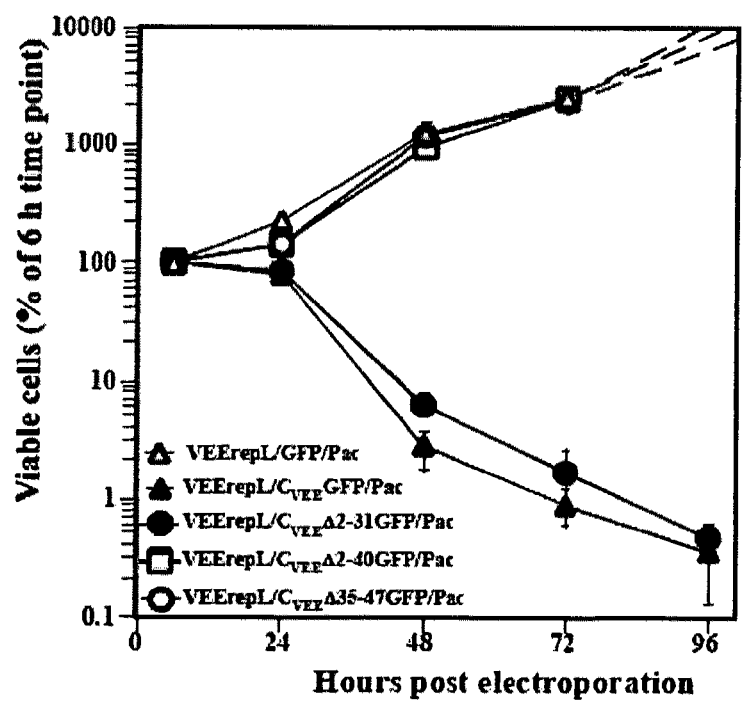

Further, the fragment encoding the peptide upstream of the HI (aa 2-31), the upstream fragment and a part of the HI (amino acids 2-40) and the HI only (amino acids 35-47) were deleted (FIG. 5A). The first deletion did not abolish the ability of the fusion protein to cause a cytopathic effect; however, the deletions of amino acids 2-40 and 35-47 made fusion proteins completely incapable of both CPE induction (FIG. 5B) and inhibiting cellular transcription. Thus, the results strongly indicated that the entire HI is required for the capsid to be active in both processes.

Figure 6A:
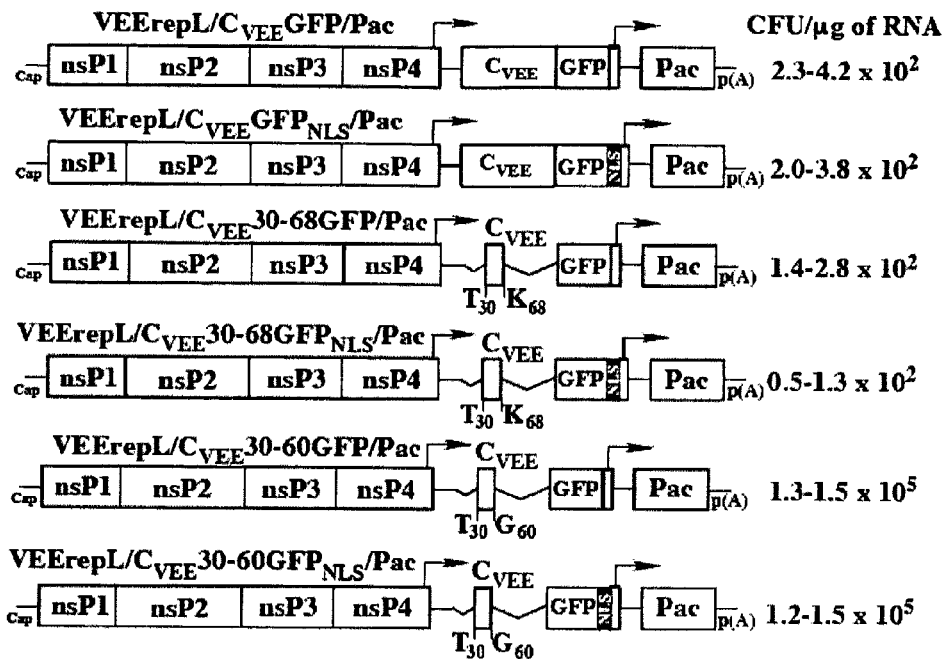
Figure 6B:
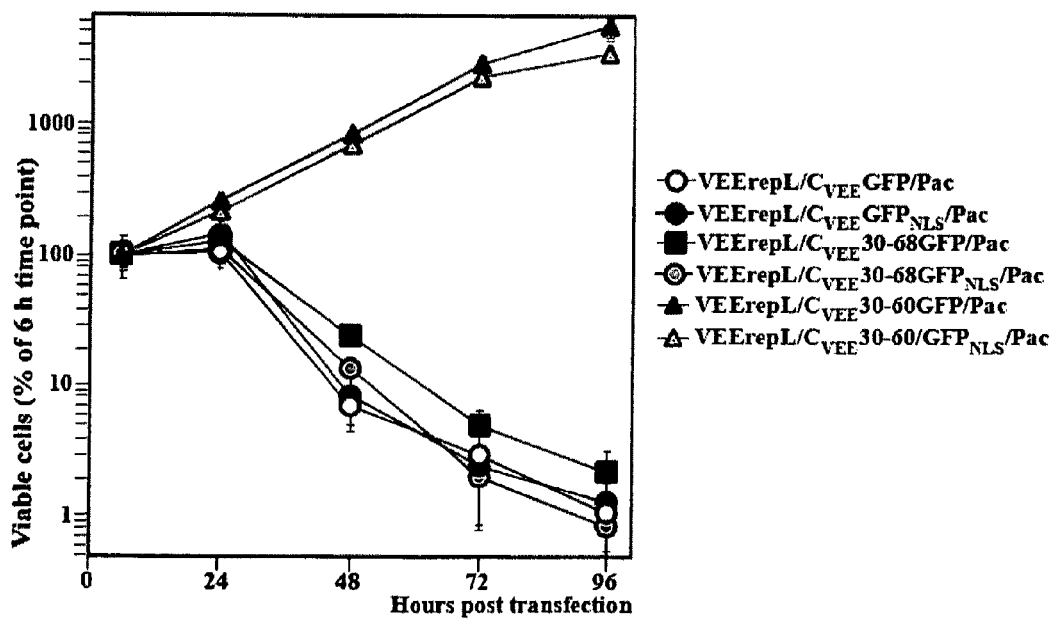

To further confirm the conclusion that the $C_{VEE}$34-68 peptide can function as the entire capsid in causing CPE cellular transcription inhibition, cassette wherein the GFP gene was fused with this minimal $C_{VEE}$30-68-coding sequence was designed. Four amino acids (amino acids 30-33) were left upstream of the HI to preserve its proper folding. An additional AUG codon was cloned upstream of the $C_{VEE}$ sequence, and fusion with GFP was performed through a flexible linker. VEErepL/$C_{VEE}$30-68GFP/Pac replicon was as cytopathic as VEErepL/$C_{VEE}$GFP/Pac (FIGS. 6A-6B), and the replicon expressing a shorter, $C_{VEE}$30-60, version of the protein did not noticeably affect cell growth. This finding could be possibly explained by the fact that the $C_{VEE}$30-60 peptide had the putative, computer-predicted NLS (aa 64-68) deleted, leading to a less efficient translocation of the protein to the nucleus. To additionally study this possibility, a standard 3xNLS was cloned into the C-terminus of the GFP of all three constructs. These NLSs did not have any effect on $C_{VEE}$30-68GFP and $C_{VEE}$GFP functioning, and did not improve the ability of $C_{VEE}$30-60GFP to inhibit cellular transcription.

Taken together, the results of this study strongly indicated that the peptide, located between amino acids 33 and 69 of $C_{VEE}$, is critically involved in CPE development and transcription inhibition. Both the HI peptide and the downstream sequence (amino acids 52-68) are required for capsid function. The HI deletion and modifications of the downstream peptide make $C_{VEE}$30-68 nonfunctional. Moreover, the amino acids 52-68 peptide appeared to function not only as NLS, but is likely directly involved in the development of transcriptional shutoff.

EXAMPLE 12

Figures 6C, 7A:
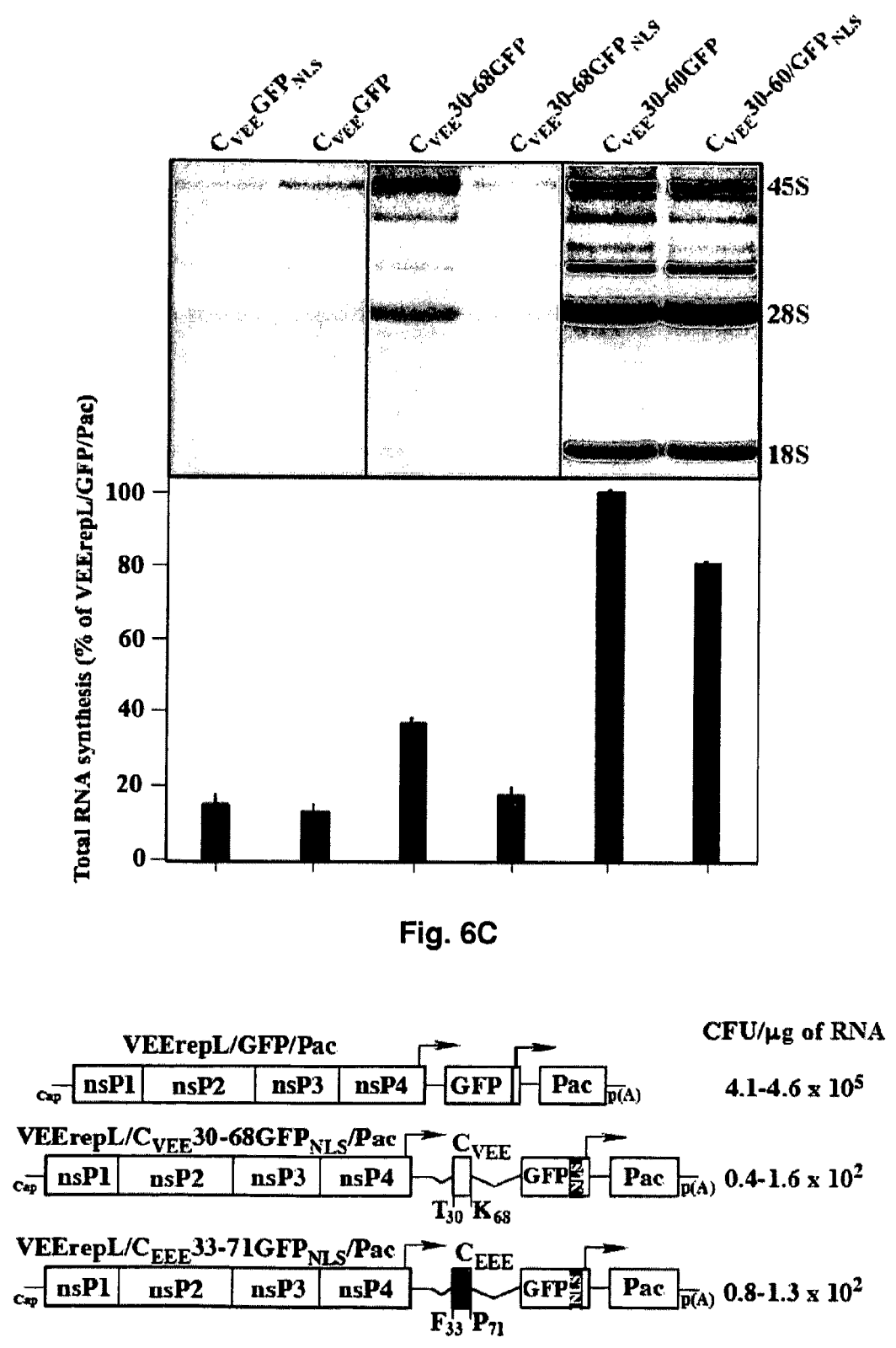
Figure 7B:
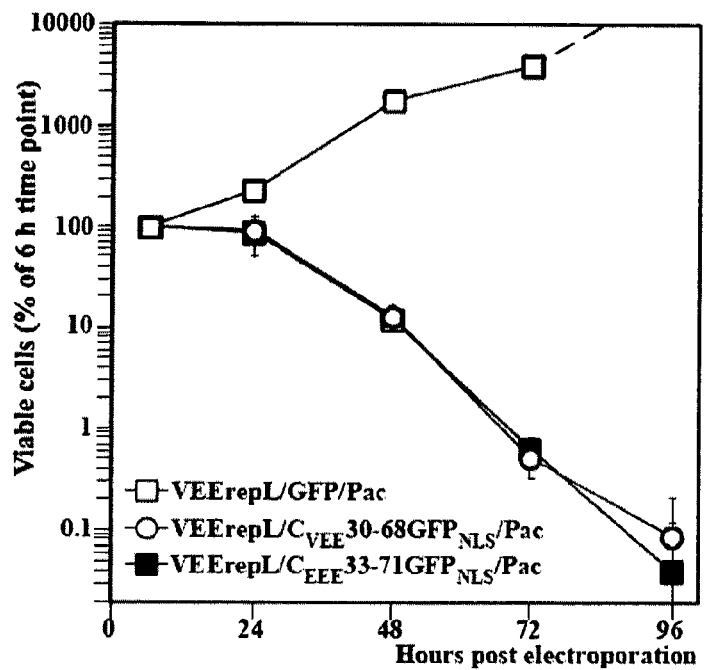
Figure 7C:
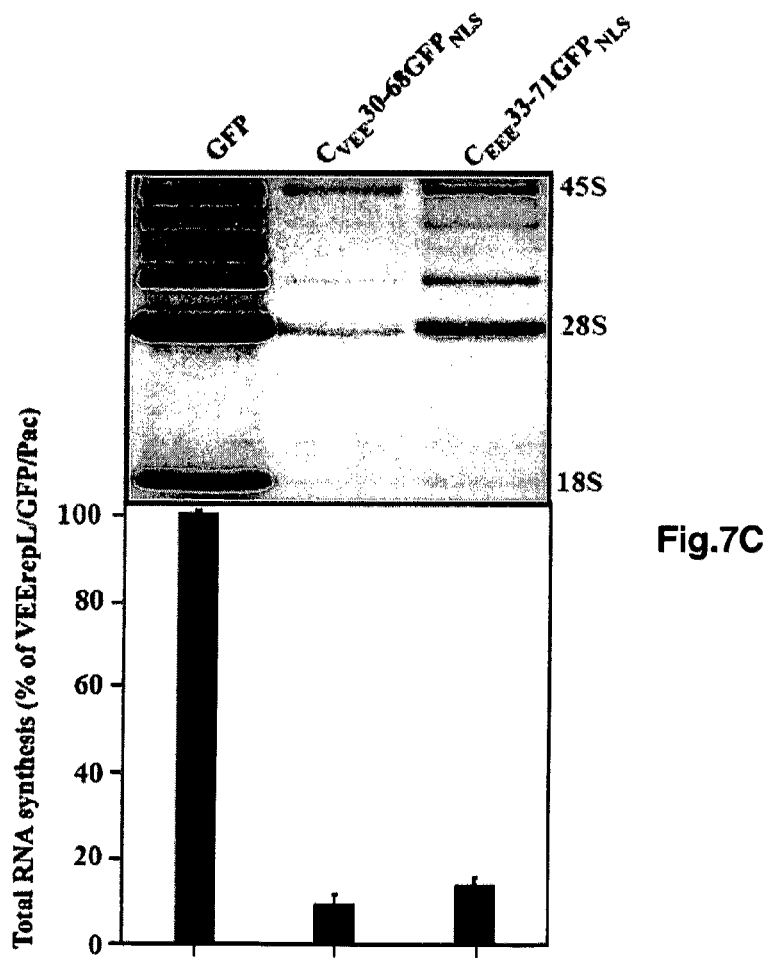

The EEEV-specific, HI-containing Peptide Functions Similar to its VEEV-specific Counterpart As described supra, the $C_{VEE}$30-68 peptide demonstrates a significant level of conservation among the New World alphaviruses (FIG. 3A). Therefore, it is reasonable to expect that it has similar mode of functioning in EEEV and WEEV. To test this possibility, amino acids 33-71 of $C_{EEE}$ (which corresponds to aa 30-68 of $C_{VEE}$ capsid) was expressed as a GFP fusion from VEErepL replicon (FIG. 7A). Since $C_{EEE}$ was not studied as intensively as $C_{VEE}$, whether the determinant of its function in transcription inhibition and the NLS are located in the same peptide (as they are in $C_{VEE}$) was not known. By this reason, an additional 3xNLS was cloned into the C terminus of GFP of $C_{EEE}$33-71GFP fusion. After transfection of the in vitro-synthesized RNAs, cells expressing $C_{EEE}$33-71GFP$_{NLS}$ fusion demonstrated the same rates of CPE development as did those with $C_{VEE}$30-68GFP$_{NLS}$ (FIG. 7B), and transcription in these cells was inhibited to the same level (FIG. 7C). This result strongly indicated that the ability to interfere with the transcription of cellular RNAs is a feature of the same peptide in capsid proteins derived from the New World alphaviruses, and this group of viruses appears to employ similar mechanisms of interference with cellular gene expression.

EXAMPLE 13

Intracellular Distribution of VEEV Capsid

As demonstrated previously, $C_{VEE}$ is distributed not only in the cytoplasm, but also in the nuclei of virus-infected cells (12). Its presence in the nucleus might be determined by a combination of active nuclear import and passive diffusion. Based on computer predictions, this protein appears to contain a number of NLS-like sequences that might promote its transport into the nucleus, and the majority of these putative signals is concentrated within the peptide between amino acids 57-86, which was changed by two attenuating, frame-shift mutations (12) (VEErepL/$C_{VEE}$frsh/Pac in FIG. 1B). These data indicated that the putative NLS(s) might be functional and important for $C_{VEE}$ activity in the inhibition of transcription. Additionally to investigate this, the intracellular distribution of $C_{VEE}$GFP and $C_{VEE}$frshGFP fusions expressed by VEErepL replicons was compared. These fusion proteins are too large for passive diffusion through the nuclear pores (30), and their presence in the nucleus should be determined by NLS-dependent, active transport. The results presented in FIG. 8A demonstrate that a significant fraction of $C_{VEE}$GFP was transported into the nucleus, and the amino acids 58-85-frame-shift mutation blocked the ability of the protein to accumulate in the nucleus and on the nuclear membrane.

Figure 8A:
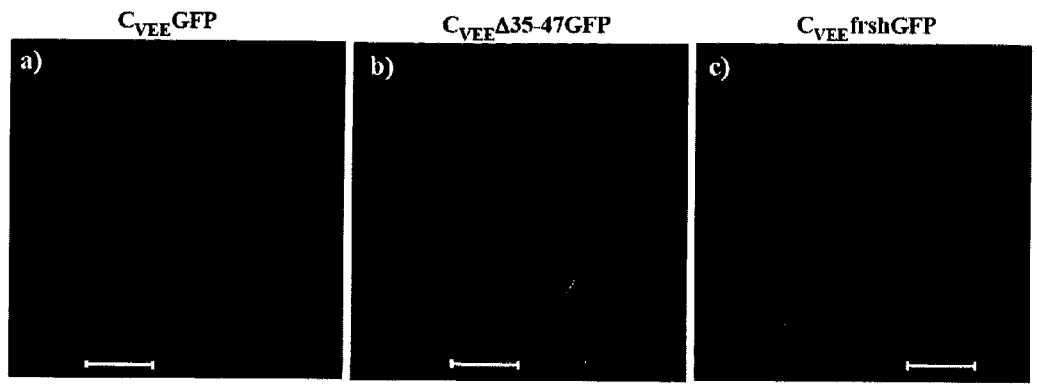
FIGS. 8A-8B show intracellular distribution of different $C_{VEE}$GFP fusions.

The presence of active NLS(s) in the capsid protein raised the issue of whether this protein does not completely concentrate in the nucleus. Its presence in the cytoplasm might certainly be explained by binding to the ribosomes and/or core assembly. However, the study of the intracellular distribution of another $C_{VEE}$GFP mutant suggested an alternative explanation. $C_{VEE}$GFP fusion that had an HI deleted (VEErepL/$C_{VEE}$D35-47GFP/Pac replicon in FIG. 5A) accumulated only in the nuclei of the transfected cells (FIG. 8A). This was an indication that the HI is either i) required for binding of capsid to cytoplasmic organelles, ii) it stimulates an immediate assembly of capsid molecules into higher-order, core structures, or iii) it functions as a nuclear export signal supporting the balance between the nuclear and cytoplasmic capsid concentrations.

The more detailed analysis of $C_{VEE}$GFP compartmentalization revealed another interesting feature of this protein. Significant fractions of $C_{VEE}$GFP (FIG. 8B) and $C_{VEE}$30-68GFP fusions were detected in the nuclear rim, where both proteins demonstrated a punctuated pattern of distribution reminiscent of that of the nuclear pore complexes (NPC). Cells expressing this fusion protein from VEErepL replicon were stained with nuclear pore-specific antibody (Mab414), which recognizes the conserved FxFG repeats in several nucleoporins, namely Nup62, Nup98, Nup153, Nup214 and Nup358. By using confocal microscopy, co-localization of $C_{VEE}$GFP was demonstrated with the Mab414 stained NPCs. In addition, some large, $C_{VEE}$GFP-containing complexes that were also capable of Mab414-binding were detected in the cytoplasm. It is speculated that these structures are the annulate lamellae (22) that were shown to contain nuclear pore-like complexes. Thus, the results presented herein indicate that the wt capsid and its $C_{VEE}$30-68 variant are capable of binding to NPC. Alterations of HI or replacement of the HI-containing fragment by that of SINV capsid abolished localization of fusion proteins on the nuclear membrane.

EXAMPLE 14

Attenuated VEEV Variants

Figure 9A:
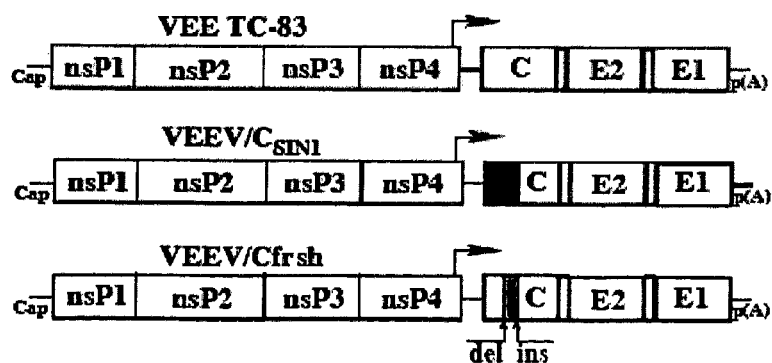

As we indicated above, $C_{VEE}$ expression by VEErepL determined the development of CPE and transcriptional shut-off in cells of vertebrate origin. However, the capsid protein of another alphavirus, SINV, was incapable of causing both phenomena. These results suggested that VEEV might be attenuated by making the extended mutations in the critical C34-68 amino acid peptide or by replacing this peptide with the corresponding $C_{SIN}$-derived fragment. Two possible variants tested herein (FIG. 9A) were designed on the basis of the VEEV TC-83 genome. The original TC-83 strain is attenuated for adult mice, but is lethal for weanling mice after i.c. inoculation. Therefore, this virus can be used for making additional genetic manipulations and analysis of their effect on pathogenesis. In VEEV/$C_{SIN1}$, the natural VEEV capsid was replaced by a chimeric version, in which the entire N-terminal fragment, located upstream of the protease domain (aa 1-110), was replaced by its SINV-specific counterpart (amino acids 1-98). The second variant, VEEV/Cfrsh, encoded the capsid with the above described frame-shift mutations that changed the peptide between amino acid 57 and 86. It should be noted that the indicated frame shift did not change the highly hydrophilic nature of the peptide and even increased the number of positively charged amino acid in the N-terminus. However, as described supra, the frame shift affected the putative NLS. Both designed, in vitro-synthesized genomes were as infectious as a control, VEEV TC-83 RNA and generated homogeneous plaques in the infectious center assay, a finding indicating that no additional mutations were required for virus viability. In BHK-21 cells, both viruses demonstrated growth rates comparable to those of VEEV TC-83 (FIG. 9B); however, in contrast to TC-83, they became non-cytopathic, and did not stop cell growth, while infected cells were incubated in the media supplemented with 10% FBS. Nevertheless, they were still capable of forming plaques in BHK-21 cells under agarose cover having low serum concentration.

Figures 9B, 9C:
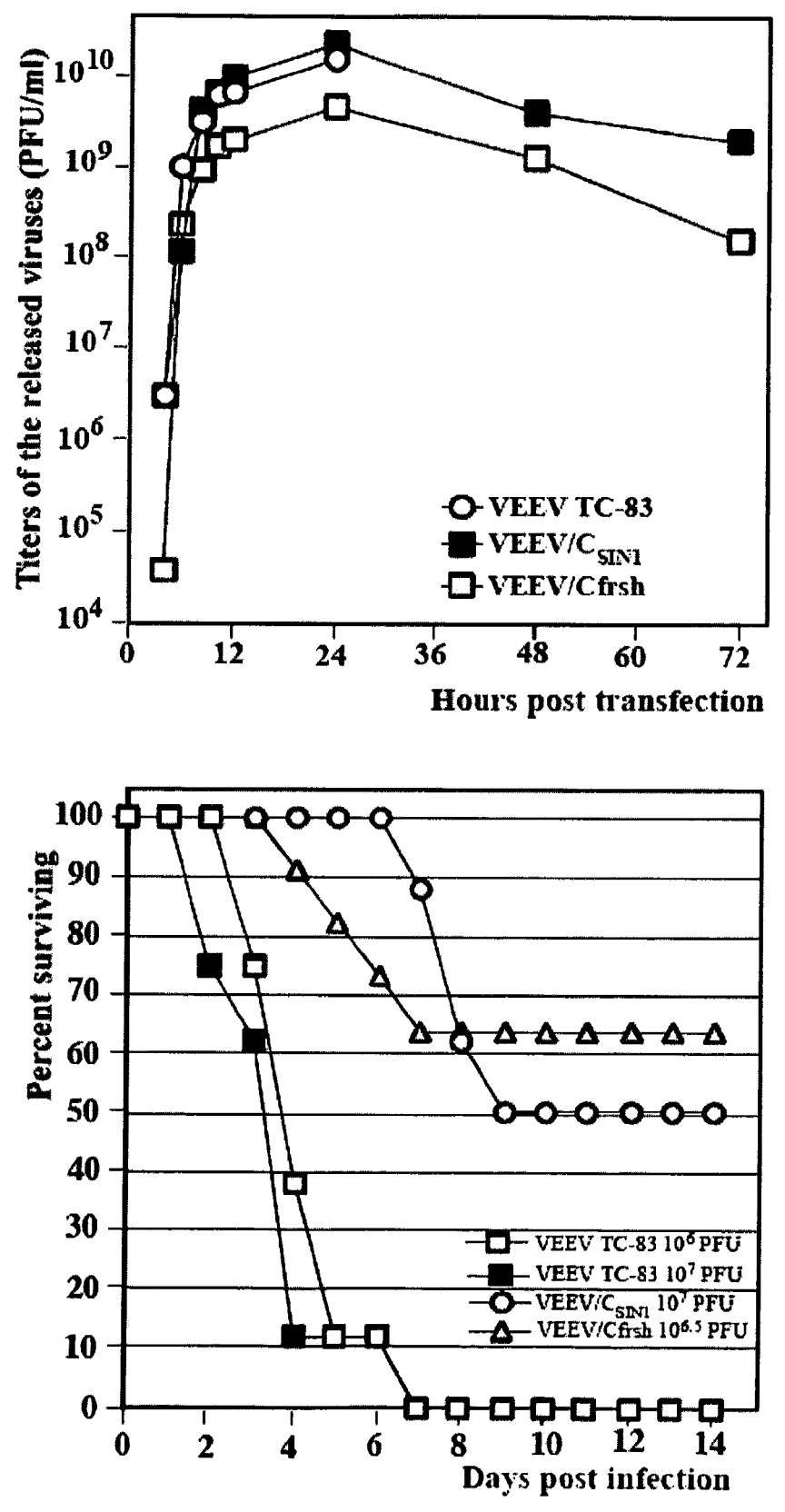

Harvested viruses were further tested for their pathogenicity in suckling mice. Animals were i.c. inoculated with $10^7$ PFU of VEEV/$C_{SIN1}$, VEEV/Cfrsh and two indicated doses of VEEV TC-83 (FIG. 9C). Both doses of the latter virus were universally lethal for mice of this age. VEEV/$C_{SIN}$ and VEEV/Cfrsh caused death only in part of mice, in spite of our having used very high doses. Thus, modification of $C_{VEE}$ by replacing the amino terminal fragment with the SINV-specific counterpart or by a frame-shift mutation, affecting the NLS, caused an additional attenuation of the VEEV TC-83. These data demonstrated the importance of $C_{VEE}$ and the identified peptide $C_{VEE}$34-68, in particular, for virus replication and pathogenesis.

The present invention also investigated the effect of $C_{VEE}$ on nucleocytoplasmic transport and demonstrated that i) both VEEV capsid and its active peptide (aa 33-68), block multiple nuclear import pathways, but do not noticeably affect the passive diffusion of small proteins from the cytoplasm to the nucleus. ii) This activity is specific for $C_{VEE}$, but not for the capsid derived from the Old World alphavirus, Sindbis virus (SINV). iii) $C_{VEE}$ expression does not noticeably affect nuclear import in the cells of mosquito origin. This inability to affect nuclear traffic provides one of the plausible explanations for lack of profound cytopathic effect (CPE) in the VEEV-infected arthropod cells and persistent, life-long replication of VEEV in the mosquito vectors without noticeable effect on their biological functions.

EXAMPLE 15

Cell Cultures

BHK-21 cells were obtained from Dr. Paul Olivo (Washington University, St. Louis, Mo.). NIH 3T3 cells were obtained from the American Type Tissue Culture Collection (Manassas, Va.). HEK293 cells were provided by Dr. Robert Davey (University of Texas Medical Branch at Galveston). These cell lines were maintained at 37° C. in alpha minimum essential medium (aMEM) supplemented with 10% fetal bovine serum (FBS) and vitamins. Mosquito $C_710$ cells were obtained from Dr. Henry Huang (Washington University, St. Louis, Mo.). They were propagated in DMEM supplemented with 10% heat-inactivated FBS and 10% tryptose phosphate broth (TPB).

Plasmid Constructs pVEErep/4xTomato plasmid encoded the VEEV replicon, in which two tdTomato gene were fused in frame through a short linker GHGTGSGGSGSS (SEQ ID NO: 5), which was previously applied for tandem cloning of other fluorescent proteins, and the entire cassette was cloned under control of the subgenomic promoter of the replicon. The tdTomato encodes a dimer of modified DsRed, and, thus, the entire cassette was designated a 4xTomato to emphasize that this is a tetrameric protein. Further modifications of this expression cassette, which were aimed at fusing the 4xTomato with different nuclear localization signals (NLSs), were made by using PCR or by cloning the sequences that were designed from the oligonucleotides. pVEErep/$C_{VEE}$/GFP encoded VEEV replicon, in which one of the subgenomic promoters controlled the expression of VEEV capsid, and the second promoter drove GFP expression. The expression of this marker was used for demonstrating the presence of the replicon in the cells. pVEErep/$C_{SIN}$/GFP had the same design, but encoded a SINV capsid protein ($C_{SIN}$) under the control of the subgenomic promoter. pVEErep/$C_{VEE}$-GFP contained a VEEV replicon having only one subgenomic promoter that drove the expression of the $C_{VEE}$-GFP fusion protein. To avoid cleavage, the last aa in $C_{VEE}$ was deleted, and fusion was performed through the short linker peptide $(Gly)_4$. pVEErep/$C_{VEE}$1-68-GFP and pVEErep/$C_{VEE}$frsh-GFP had a similar design, but encoded in the fusion protein only the aa 1-68 of VEEV capsid or $C_{VEE}$ with previously identified, frame-shift mutations (18), affecting aa 58-85. The latter frame-shift mutations made the capsid incapable of causing transcriptional shutoff and CPE development. pSINrep2V/Ubi-nsP2$_{VEE}$-HA encoded a SINV replicon that had a mutation in the nsP2/nsP3 cleavage site, and the subgenomic promoter controlled the expression VEEV nsP2, tagged with HA sequence. This replicon was incapable of P23 processing, and, thus, the unprocessed SINV nsP2 did not interfere with VEEV nsP2 transport into the nucleus. Ubi was used to promote expression of VEEV nsP2 with natural Ala at the amino terminus. pVEErep/Cherry contained a VEEV replicon that encoded one of the red fluorescent proteins, Cherry, under the control of the subgenomic promoter. All of the above-described, VEEV and SINV replicon-based cassettes were synthesized by PCR-based techniques, and all of heterologous genes were sequenced. All of the constructs that we used are presented in the corresponding figures. Sequences of the recombinant plasmids can be provided upon request. VEEV and SINV helpers used for replicons' packaging.

Viruses

Vaccine strain VEEV TC-83 and SINV Toto1101were rescued from the infectious cDNA clones. VEEV/nsP2GFP virus was developed by random GFP insertion mutagenesis using the same strategy as described for SINV. The GFP insertion was made after aa 3 of nsP2 gene in VEEV TC-83 genome, and, in contrast to similar SINV constructs, this additional sequence had only a minor effect on the efficiency of P123 cleavage. SIN/VEEV chimeric virus encoded the SINV-derived 5' and 3' UTRs, the subgenomic promoter and nsPs, but the structural genes were VEEV TRD-specific and had additional mutations, adapting this virus to efficient growth in BHK-21 cells.

RNA Transcriptions

Plasmids were purified by centrifugation in CsCl gradients, and linearized using the MluI restriction site located downstream of the poly(A) sequence of the VEEV replicons and helper-encoding plasmids. RNAs were synthesized by using SP6 RNA polymerase in the presence of a Cap analog. The yield and integrity of transcripts were analyzed by gel electrophoresis under non-denaturing conditions. RNA concentration was measured on a Fluor Chem imager (Alpha Innotech), and transcription reactions were used for electroporation without additional purification.

Packaging of the Replicons

BHK-21 cells were co-electroporated with the in-vitro-synthesized SINV replicon and BBdel/SL2/C and BBdel/SL2/GI helper RNAs or by VEEV replicon and Hvee/C and Hvee/GI helper RNAs (56). The indicated helper RNA encode either capsid or viral glycoproteins and contain no packaging signal(s). They are packaged into viral particles very inefficiently. Packaged replicons were harvested at 24-30 h post electroporation. Titers of the replicon-containing, infectious virus particles were determined by infecting BHK-21 cells with serially diluted samples. Cells were further incubated for 16 h at 30° C. in a $CO_2$ incubator, and numbers of infected cells were determined under an inverted, fluorescent microscope by counting 4xTomato-, Cherry- or GFP-positive cells. Titers of the infectious VEEV TC-83 and VEEV/nsP2GFP were determined using the standard plaque assay.

Analysis of Protein Synthesis

BHK-21 cells were seeded into six-well Costar plates at a concentration of $5\times10^5$ cells/well. After 4 h incubation at 37° C. in 5% $CO_2$, they were infected at an MOI of 20 PFU/cell or 20 infectious units (inf.u)/cell of viruses or packaged replicons, respectively, in 500 ml of alpha MEM supplemented with 1% FBS at room temperature for 1 h with continuous shaking. The medium was then replaced by a corresponding complete medium, and incubation continued at 37° C. At 8 h post infection, the cells were washed three times with phosphate-buffered saline (PBS) and then incubated for 30 minutes at 37° C. in 0.8 ml of DMEM medium lacking methionine, supplemented with 0.1% FBS and 20 mCi/ml of [$^{35}$S] methionine. After this incubation, cells were scraped into the media, pelleted by centrifugation and dissolved in 200 ml of standard protein loading buffer and loaded onto sodium dodecyl sulfate-10% polyacrylamide gels. After electrophoresis, gels were dried and autoradiographed.

Microscopy

BHK-21 cells were seeded on glass chamber slides (Nunc) and infected or co-infected by the packaged replicons for 1 h. Incubation was continued for 8 h at 37° C. in a $CO_2$ incubator. Then cells were fixed in phosphate buffered saline (PBS), supplemented with 4% formaldehyde, and the distribution of the proteins was analyzed on a Zeiss LSM510 META confocal microscope using a 63×1.4NA oil immersion planapochromal lens. For staining of VEEV nsP2, cells were permeabelized with 0.5% Triton X-100 and stained with anti-VEEV nsP2 antibodies, provided by AlphaVax (Research Triangle Park, NC) (used at 1:2000 dilution). After staining with AlexaFluor 488-labeled secondary antibodies (Invitrogen), cells were analyzed via confocal microscopy. These goat anti-VEEV nsP2 antibodies demonstrated considerable staining of the nuclei in the mock-infected cells. Therefore, before immunostaining, they were pre-absorbed on the lysate of BHK-21 cells. $2\times10^7$ cells were used for pre-adsorption of 1 ml of the antiserum. Cells were pelleted by low-speed centrifugation, permeabelized with 0.5% Triton-X100 and additionally homogenized through a syringe needle. Pre-absorption was performed for 1 h at room temperature with continuous shaking. Then cell debris was removed by centrifugation at 16,000×g and the supernatant was used for cell staining as described above. Staining with affinity-purified, rabbit anti-SINV nsP2 (1:2000) and anti-HA (1:200) (Covance) antibodies was performed using the same protocol, but the pre-adsorption step was omitted.

EXAMPLE 16

Results

Figure 10A:
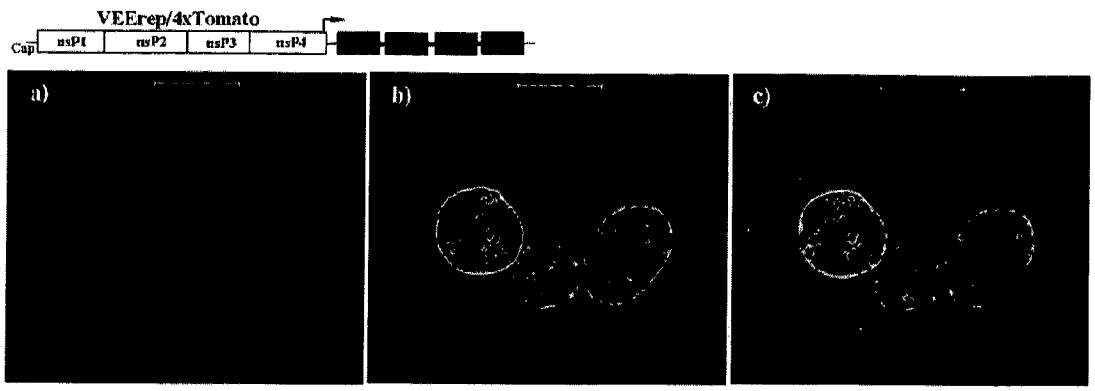
FIG. 10A-C shows downregulation of the importin-a/b-mediated nuclear import in the cells infected with VEEV TC-83. BHK-21 cells were either infected with packaged VEErep/4xTomato (FIG. 10A) or VEErep/4xTomato-3xNLS (FIG. 10B) replicons at an MOI of ~20 inf.u/cell, or co-infected with VEErep/4xTomato-3xNLS replicon and VEEV TC-83 at the same MOIs (FIG. 10C). Distribution of 4xTomato and 4xTomato-3xNLS proteins was evaluated at 8 h post infection. Panels: (a) distribution of the 4xTomato and 4xTomato-3xNLS proteins; (b) cell nuclei stained with SYTOX Green (Invitrogen); (c) overlay of two images. Schematic representations of used VEErep/4xTomato and VEErep/4xTomato-3xNLS replicons and VEEV TC-83 genome are shown. Bars correspond to 20 mm.

VEEV infection inhibits nuclear import. The presence of $C_{VEE}$ on the nuclear membrane was identified suggesting the possibility that this protein might affect nucleocytoplasmic trafficking, and, thus, interfere with the expression of cellular genes. Therefore, an experimental system for analysis of inhibition of the nuclear import was developed by designing a VEEV replicon encoding a high-molecular-weight fluorescent protein that could not translocate into the nucleus by passive diffusion and whose presence in the nucleus could be achieved only by active, importin-dependent transport through the nuclear pores. It was believed that only the proteins having a molecular weight below 40-50 kDa could migrate into the nuclei by passive diffusion, which is mediated by different channels in the nuclear pore complex (NPC). However, the maximum size of the proteins that are capable of diffusing through the NPC could be larger than 60 kDa. Therefore, a 4xTomato protein which had a molecular weight of 109.5 kDa was designed, and it was cloned into the VEEV replicon under control of the subgenomic promoter. Upon delivery into BHK-21 cells by electroporation, the expressed 4xTomato was detected only in the cytoplasm (FIG. 10A (1A of paper). Then, in the following experiments, this protein was fused with a variety of the NLS sequences. These modified genes were also cloned into the VEEV replicon (VEErep) under control of the subgenomic promoter, and the replicons were packaged into infectious viral particles by using the previously described two-helper system.

Figure 10B:
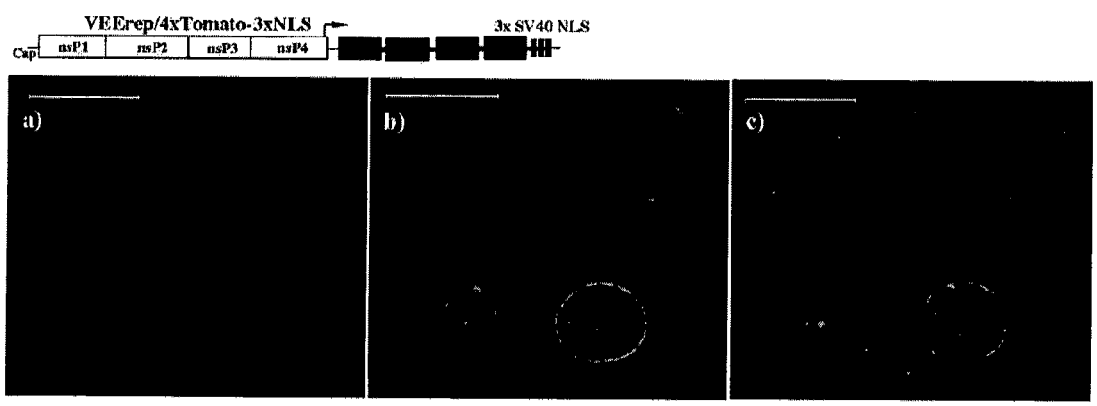
Figure 10C:
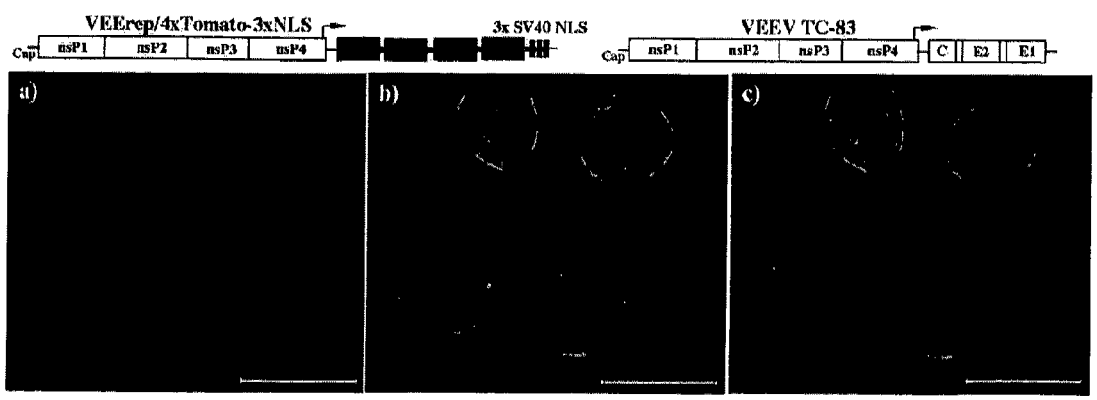

The first tested expression cassette contained a triple SV40 TAg-derived NLS (VEErep/4xTomato-3xNLS) (FIG. 10B (FIG. 1B of paper)), which is known to interact with importin-a/b complexes, mediating nuclear import of about 57% of the cellular proteins. In initial experiments, that inhibition of nuclear import is a biological phenomenon that occurs in VEEV-infected cells was demonstrated. Therefore, BHK-21 cells were either infected with packaged VEErep/4xTomato-3xNLS replicon (FIG. 10B) or co-infected with this replicon and VEEV TC-83 (FIG. 10C). In the cells infected only with packaged replicon, the 4xTomato-3xNLS protein accumulated to high concentrations in the cell nuclei (FIG. 10B), and in some cells, formed additional aggregates in the cytoplasm. Co-infection with VEEV TC-83 completely blocked the translocation of the protein to the nucleus (FIG. 10C). At 8 h post infection, the 4xTomato-3xNLS was detected only in the cytoplasm of the infected cells. These experiments demonstrated that VEEV infection inhibits the nuclear import, mediated by SV40 TAg-derived NLS. The ability of the 4xTomato-3xNLS to accumulate in the nucleus, when expressed from VEEV replicon, also indicated that VEEV nsPs do not block nuclear import.

Figure 11A:
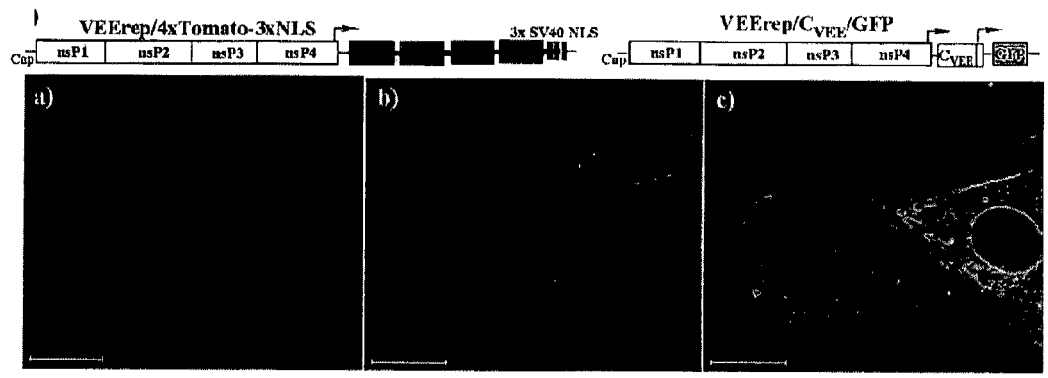
FIG. 11A-11D shews the expression of $C_{VEE}$ affects nuclear import of the proteins having different nuclear localization signals.

VEEV capsid inhibits multiple nucleocytoplasmic transport pathways. The above-described experiments indicated that VEEV structural proteins function in the inhibition of nuclear import. Moreover, it was reasonable to expect that the VEEV capsid, but not the envelope glycoproteins, plays a critical role in this process. Therefore, in successive experiments, whether $C_{VEE}$ affects nucleocytoplasmic trafficking was examined, and it was distinguished whether it inhibits only the receptor-mediated nuclear import pathways or blocks passive diffusion of small proteins as well. Inhibition of active, so-called classical nuclear import pathway was analyzed using the above-described VEEV replicon, expressing the 4xTomato-3xNLS reporter protein (FIG. 11A). The second replicon encoded a small GFP protein (having a molecular weight of 27 kDa) under the control of the subgenomic promoter, and another subgenomic promoter was driving the expression of the VEEV capsid. GFP was used for two reasons: i) its expression in the cells indicated the presence of the $C_{VEE}$-expressing replicon, and ii) the analysis of the intracellular distribution of the GFP provided information about whether passive diffusion of small proteins to the nucleus was affected by the co-expressed, tested proteins. The rationale for application of VEEV replicons for expressing capsid and its derivatives instead of using more traditional RNA polymerase II promoter-based expression cassettes was based on the fact that that VEEV- and EEEV-derived capsids efficiently inhibit nuclear transcription. Therefore, their expression from plasmid DNA-based cassettes could be problematic.

Figure 11B:
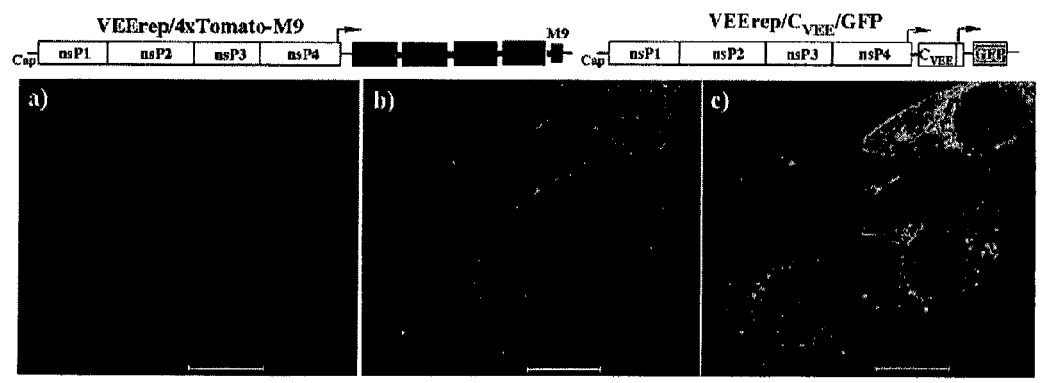
Figure 11C:
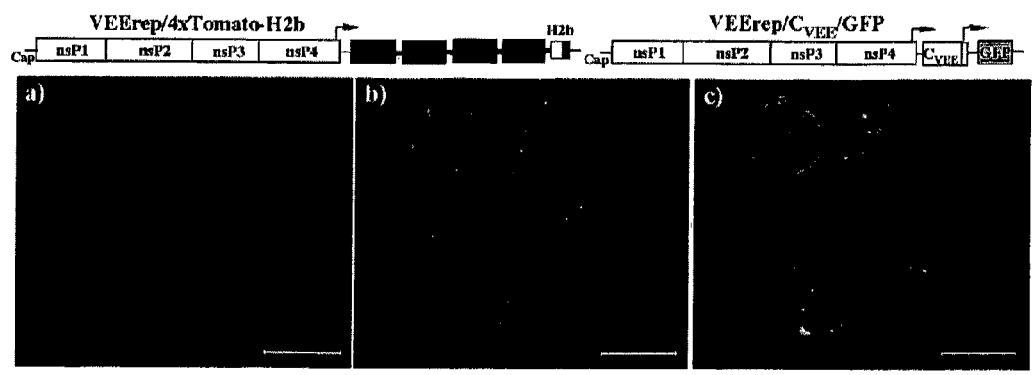
Figure 11D:
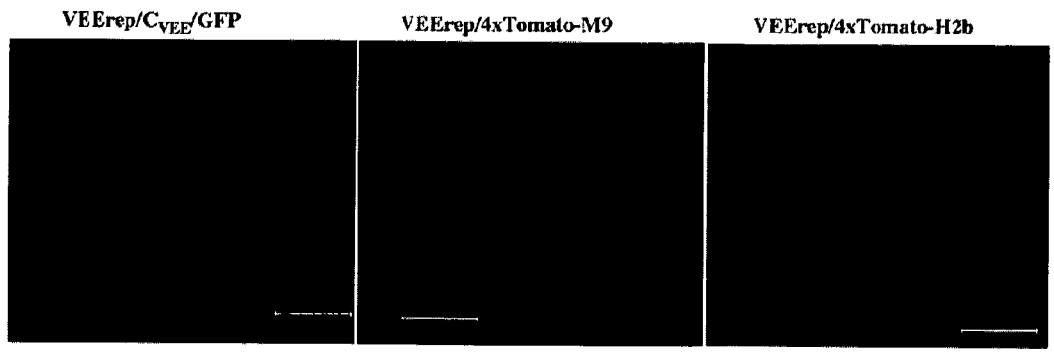
Figure 12:
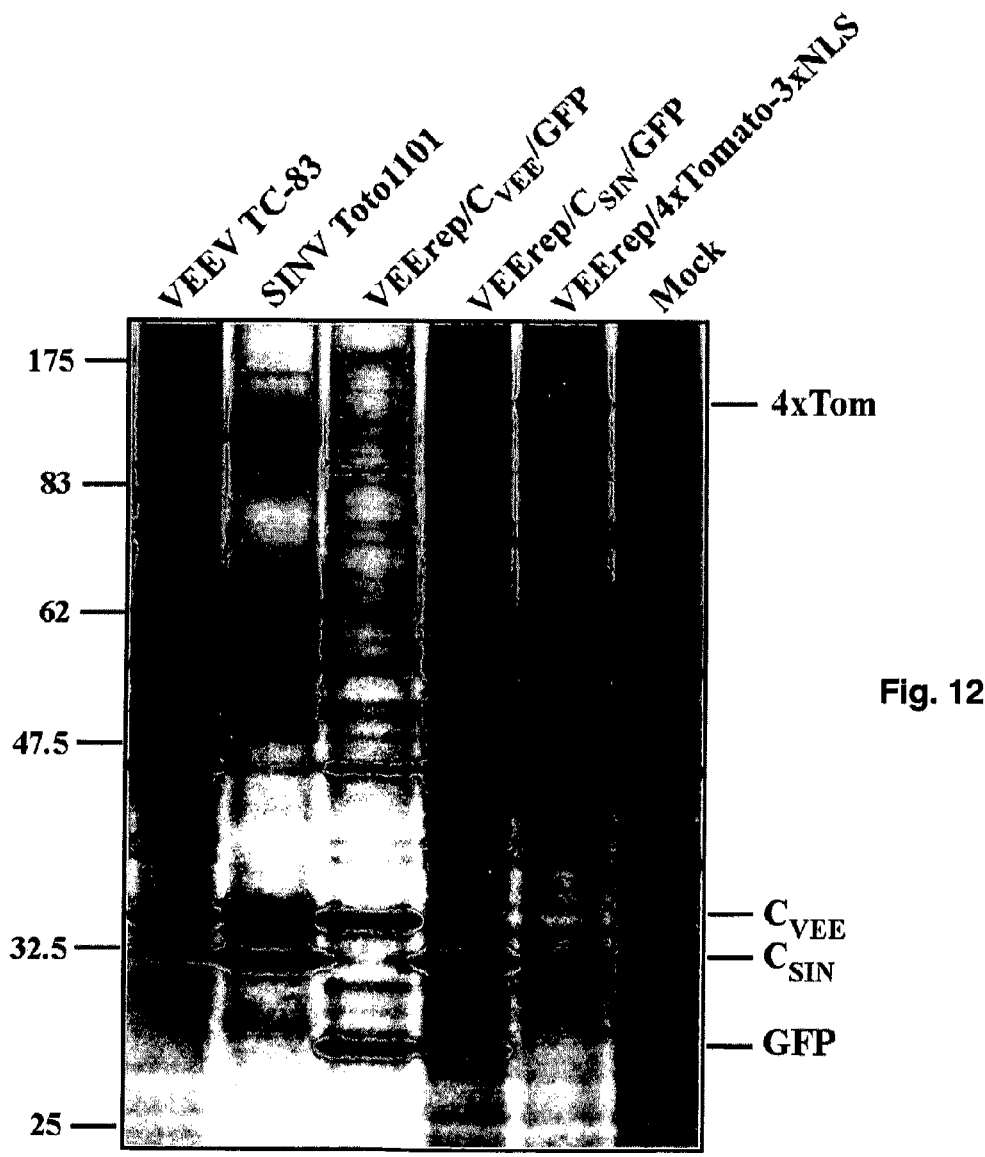
FIG. 12 shows 5×10$^5$ BHK-21 cells in 6-well Costar plates were infected with the indicated replicons and viruses at an MOI of 20 inf.u or PFU per cell, respectively. Proteins were pulse-labeled with [$^{35}$S]methionine at 8 h post infection and analyzed on sodium dodecyl sulfate-10% polyacrylamide gel. Gel was dried and autoradiographed. Positions of the expressed proteins of interest are indicated at the right side of the gel.

Both $C_{VEE}$- and 4xTomato-3xNLS-coding replicons were packaged into infectious viral particles, and BHK-21 cells were infected separately with VEErep/4xTomato-3xNLS and VEErep/$C_{VEE}$/GFP or with both replicons together. In the VEErep/$C_{VEE}$/GFP-infected cells (see FIGS. 11A-D), GFP was distributed in the cytoplasm and the nucleus, indicating that $C_{VEE}$ expression did not noticeably affect the passive diffusion of GFP, and, most likely, other small proteins through the nuclear pores. As described above, the 4xTomato-3xNLS was concentrated in the nuclei of the cells, infected with the VEErep/4xTomato-3xNLS-expressing replicons. However, when the same protein was produced in the cells, co-infected with $C_{VEE}$-encoding replicons, it was no longer transported into the nucleus and remained only in the cytoplasm. This was a strong indication that $C_{VEE}$ inhibits at least an importin-a/b-dependent nuclear import pathway, which is considered to be responsible for translocation into the nucleus of more than 50% of the proteins. $IC_{VEE}$ expression from VEErep/$C_{VEE}$/GFP and the expression of reporter protein 4xTomato-3xNLS and $C_{VEE}$ derivatives, fused with GFP, was additionally confirmed by metabolic labeling of the cell proteins with [$^{35}$S]methionine, followed by analysis of the cell extracts by gel electrophoresis (FIG. 12). The proteins of interest were readily detectable on gels, and expressed at levels comparable to those of capsids, expressed by replicating viruses. To rule out a possibility that inhibition of nuclear import is a synergistic effect of VEEV nsP(s) and capsid functions, 4xTomato-3xNLS and VEEV capsid were also expressed from the T7 promoter/EMCV IRES-dependent cassettes in i) BHK-21 cells-derived cell line expressing T7 DNA-dependent RNA polymerase and ii) BHK-21 cells infected with a vaccinia virus recombinant expressing the same enzyme. In both expression systems, VEEV capsid efficiently inhibited nuclear import of 4xTomato-3xNLS. Thus, the capsid protein itself can interfere with nuclear import.

However, the detected blockage of importin-a/b-dependent nuclear import does not necessarily indicate that the transport of all of the proteins is affected. Therefore, the function of two other, M9- and histone H2b-specific, pathways were evaluated in the presence of $C_{VEE}$. The M9 NLS, derived from hnRNPA1 is recognized by transportin that mediates nuclear transport of the RNA-binding proteins. H1stone H2b utilizes multiple nuclear import pathways, mediated by importin-a/b complex, transportin, importin 5, importin 7, importin 7/importin b complex and importin 9. Application of this reporter allows detection of alterations in the nuclear import pathways other than SV40 TAg NLS- or M9-dependent.

Thus, both M9- and the entire mouse H2b histone-coding sequences were cloned into the carboxy terminus of the 4xTomato gene. Modified replicons, VEErep/4xTomato-M9 and VEErep/4xTomato-H2b were packaged into the infectious viral particles, and, after infection of BHK-21 cells, both peptides demonstrated efficient functioning in the translocation of the 4xTomato into the nucleus (FIG. 11D). However, the M9 NLS was noticeably less efficient than was the triple SV40 TAg NLS and H2b protein, and a significant fraction of the 4xTomato-M9 reporter remained in the cytoplasm (FIG. 11D). In the cells, co-infected with the 4xTomato-encoding replicons and the replicon expressing $C_{VEE}$, both 4xTomato-M9 and 4xTomato-H2b proteins were not transported into the nucleus (FIGS. 11B and C). These data indicate that $C_{VEE}$ is capable of inhibiting nuclear import mediated by at least three different types of NLSs, and, most likely, its presence in the cells strongly affects the entire nuclear import.

Figure 13A:
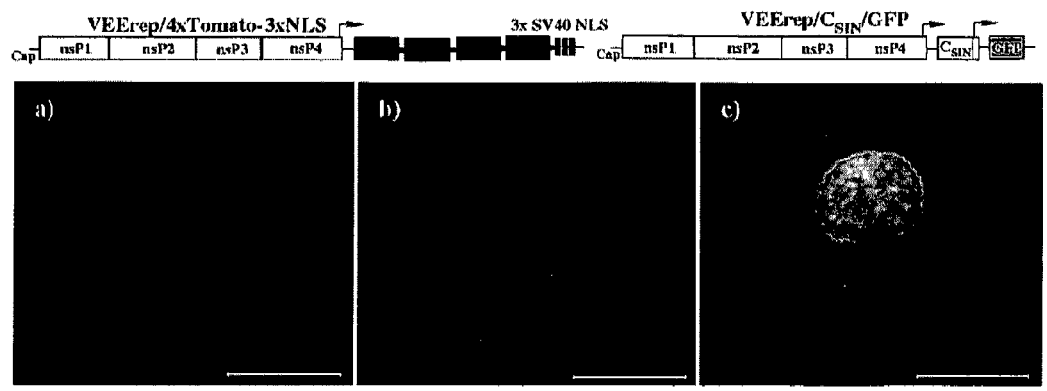
FIG. 13A-13D shows an analysis of the 4xTomato-3xNLS distribution in the cells, expressing either $C_{SIN}$ or different variants of $C_{VEE}$, fused with GFP.

SINV capsid expression does not affect nuclear import. The capsid protein of the Old World alphaviruses, SINV and SFV, is incapable of inhibiting cellular transcription and causing CPE, in spite of being present in the nuclei. To further dissect the differences between the New World and the Old World alphavirus capsid functions in virus-host cell interactions, the SINV-specific capsid ($C_{SIN}$) gene was cloned into the VEEV replicon and co-infected BHK-21 cells with this packaged VEErep/$C_{SIN}$/GFP and the described above VEErep/4xTomato-3xNLS replicons. In contrast to $C_{VEE}$, the SINV-specific capsid had no noticeable effect on the translocation of 4xTomato-3xNLS into the nuclei (FIG. 13A). The latter protein was transported to the nucleus as efficiently as in the cells infected with VEErep/4xTomato-3xNLS replicon alone. Thus, the Old World alphavirus SINV-specific capsid either causes only a minor effect on the nuclear import, (undetectable herein), or does not have this activity. Thus, its inability to interfere with the nuclear import correlates with the lack of $C_{SIN}$-specific transcriptional shutoff.

The VEEV capsid-specific N-terminal peptide plays a critical role in blocking the nucleocytoplasmic transport. The present invention identified an amino terminal peptide in $C_{VEE}$ that plays a critical role in CPE development and induction of transcriptional shutoff. This peptide, located between aa 32 and 69 of $C_{VEE}$, has two short, distinct domains: the aa 33-51, which were previously shown to fold into an a-helix secondary structure, and the downstream, positively charged aa sequence that likely contains a functional NLS. The $C_{VEE}$32-68 peptide, fused with GFP, accumulates on nuclear membrane and causes CPE as efficiently as the entire $C_{VEE}$. These data suggested that this fragment might play a critical role in the $C_{VEE}$-mediated inhibition of the nucleocytoplasmic traffic.

Figure 13B:
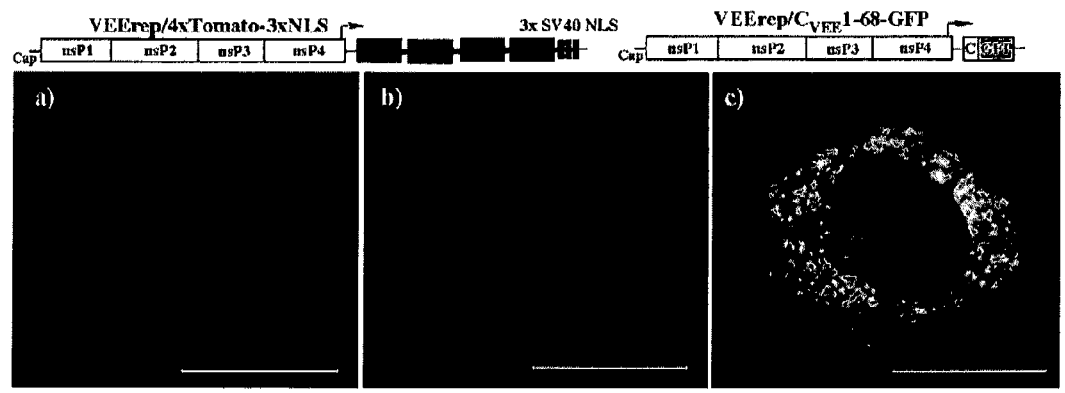
Figure 13C:
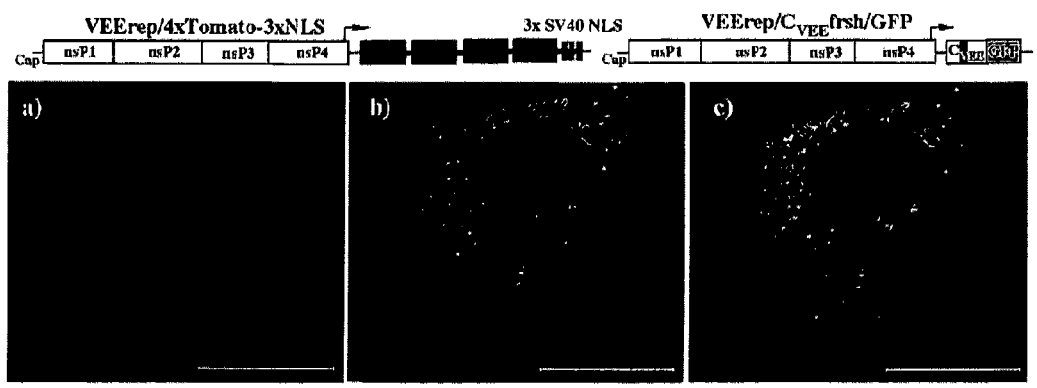

To demonstrate this, the amino terminal fragment of $C_{VEE}$ (aa 1-68), fused with GFP (VEErep/$C_{VEE}$1-68-GFP) was cloned into the VEEV replicon (FIG. 13B). The aa 1-68 sequence was applied instead of a minimal peptide to promote similar expression of this particular fusion protein and other constructs. The second replicon encoded $C_{VEE}$-GFP fusion, in which a short sequence in the $C_{VEE}$ (aa 58-85) was changed by two frame-shift mutations (FIG. 13C). This $C_{VEE}$frsh-GFP fusion, was found to be noncytopathic and incapable of inhibiting cellular transcription. VEEV replicon, encoding the entire wt $C_{VEE}$, fused with GFP (FIG. 4D), was used as a positive control.

Figure 13D:
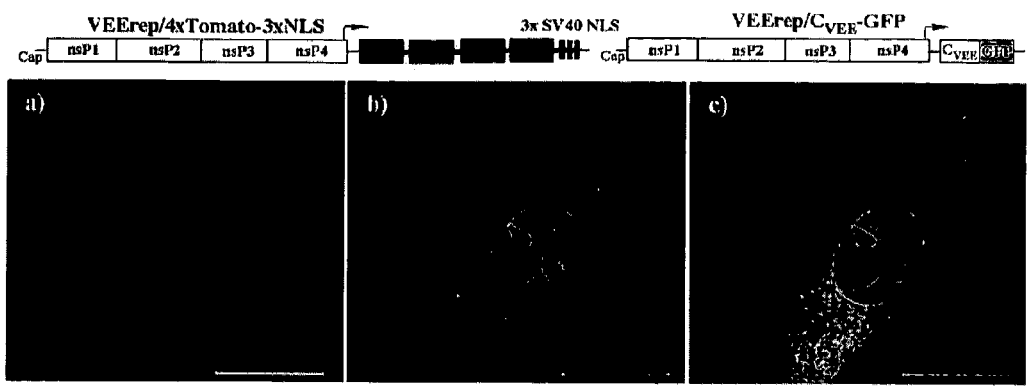

All of the replicons were packaged into infectious viral particles and used for co-infection of BHK-21 cells, together with the packaged VEErep/4xTomato-3xNLS. Expression of $C_{VEE}$1-68-GFP inhibited translocation of 4xTomato-3xNLS to the nucleus (FIG. 13B), as well as did the expression of the control $C_{VEE\text{-}GFP}$ fusion (FIG. 13D). ($C_{VEE}$1-68-GFP reproducibly formed small aggregates that might reflect its-2-fold higher level of expression, compared to those of other chimeric proteins). However, in the cells, co-infected with $C_{VEE}$frsh-GFP-producing replicon and VEErep/4xTomato-3xNLS, transport of the 4xTomato-3xNLS to the nucleus was not altered (FIG. 13C), despite the expression of both $C_{VEE}$-GFP and $C_{VEE}$frsh-GFP at very similar rates and to similar levels, which were very similar to those shown for other proteins in FIG. 12. Thus, the amino terminal sequence of $C_{VEE}$ inhibits the classical nuclear import pathway. The previously described, frame-shift mutation in $C_{VEE}$ peptide that makes this protein incapable of translocation into the nucleus and affects its ability of causing CPE and inhibiting cellular transcription also makes $C_{VEE}$ unable to block nuclear import.

VEEV nsP2 accumulates mainly in the cytoplasm. One of the nonstructural proteins, nsP2, of the Old World alphaviruses (SINV and SFV) is known to be present at a high concentration in the cell nuclei, where it functions in transcription inhibition. In the case of SINV and, most likely, of SFV, this translocation is indirectly supported by the inability of the capsid protein to interfere with the nuclear import. However, the newly described function of $C_{VEE}$ suggests that translocation of VEEV nsP2 into the nucleus might be problematic, and, in contrast to its SINV-specific counterpart, this protein is likely to accumulate in the cell nuclei at a low concentration. Data indirectly supported the possibility that VEEV nsP2 does not play a critical role in modification of the nuclear function: i) the VEEV (and EEEV) replicons were incapable of downregulating cellular transcription to a level incompatible with cell survival, and persistently replicated in some of the cell lines of vertebrate origin; ii) the VEEV variants having either the capsid or entire subgenomic RNA replaced by SINV-specific counterparts were dramatically less cytopathic than were the parental VEEV and could not interfere with the cellular antiviral response. These chimeric viruses either persisted in the cells, defective in the IFN-a/b response, or were cleared from the cells having functional IFN-a/b signaling.

To further understand the differences between the New World and the Old World alphavirus nsP2 activities in modification of the nuclear function, the distribution of VEEV nsP2, produced by different expression cassettes was analyzed and how $C_{VEE}$ interferes with the nuclear import of VEEV (and SINV) nsP2 was evaluated.

Recent data suggests that VEEV nsP2 and its fragments can be detected in the nuclei. Therefore, in order to generate definitive results, multiple cell lines and a variety of expression constructs were used to analyze the intracellular distribution of this protein. Initially, 3 cell lines, BHK-21, HEK293 and NIH 3T3 cells, were infected with VEEV TC-83 virus. The available VEEV nsP2-specific antibodies demonstrated significant staining of the nuclei in the mock-infected cells, and were pre-adsorbed in the lysate of the BHK-21 cells. After the pre-adsorption, staining of the mock-infected cells was not detectable (FIG. 14D).

Figure 14A:
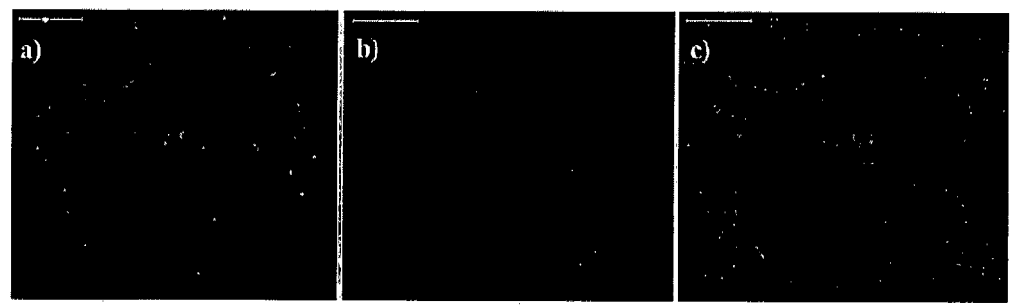
FIG. 14A-14D show the distribution of VEEV nsP2 in the cells, infected with VEEV TC-83.
Figure 14B:
Figure 14C:
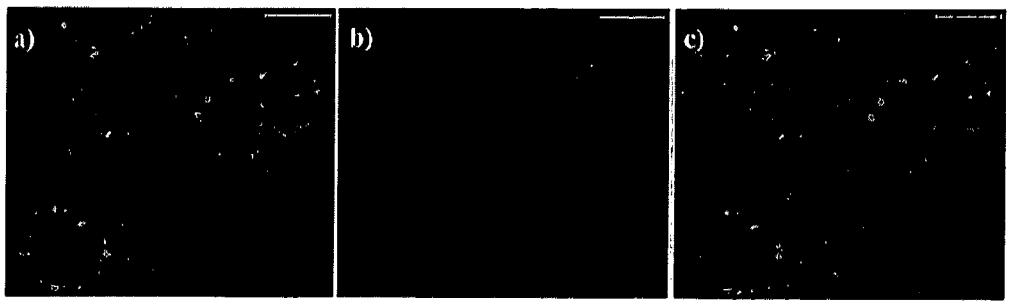
Figure 14D:
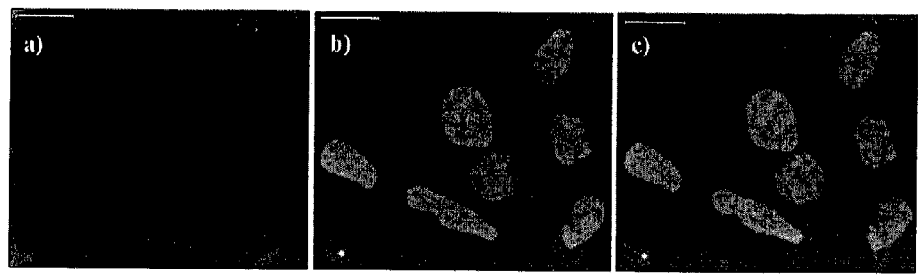

By 8 h post infection with VEEV TC-83, nsP2 was present in the nuclei of all of the tested cell lines at a very low concentration (FIGS. 14A, B and C). At later times, this protein was found at a higher concentration in the nuclei of a small percentage of the infected cells, which were already on very advanced stages of apoptosis. Thus, the presence of $C_{VEE}$, the VEEV nsP2 is unlikely to play a major role in cellular nuclei, because of its low presence in this compartment.

Figure 15A:
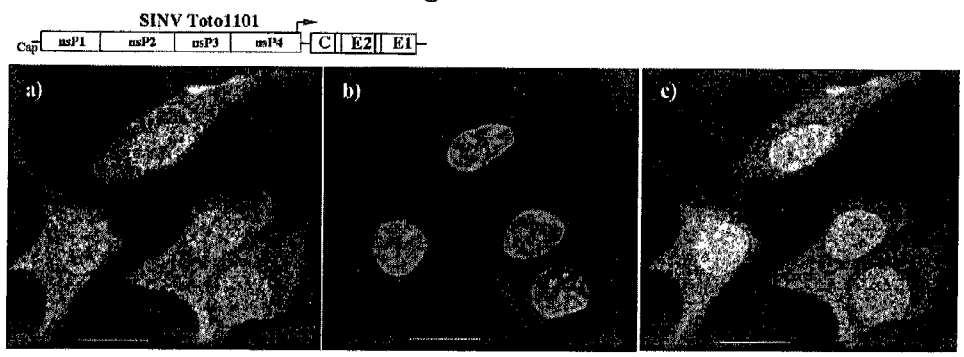
FIG. 15A-15C show that SINV nsP2 distribution depends on the capsid protein, encoded by viral genome.
Figure 15B:
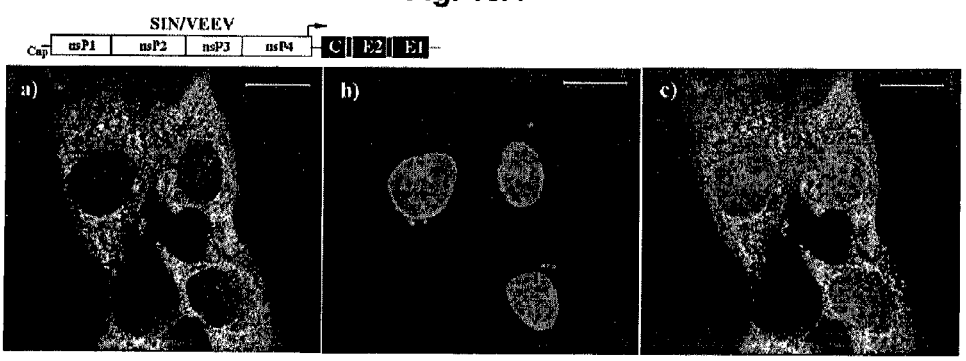
Figure 15C:
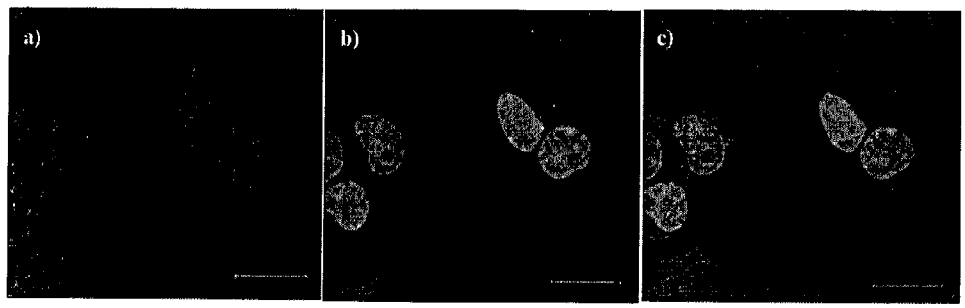

The effect of $C_{VEE}$ expression on the compartmentalization of nsP2 of different origins was evaluated. BHK-21 cells were infected either i) with the wt SINV, which encodes capsid protein that does not affect nuclear import (FIG. 15A), or ii) with SINNEEV chimeric virus that expresses all of the VEEV structural proteins (FIG. 15B). In the SINV-infected cells, SINV nsP2 was distributed both in the cytoplasm and nuclei (FIG. 15A), and in the SINNEEV-infected cells, nsP2 was detected only in the cytoplasm (its concentration in this compartment was noticeably higher than that in SINV-infected cells) (FIG. 15B). This indicated that $C_{VEE}$ expression likely interferes with SINV nsP2 translocation to the nuclear compartment.

Figure 16:
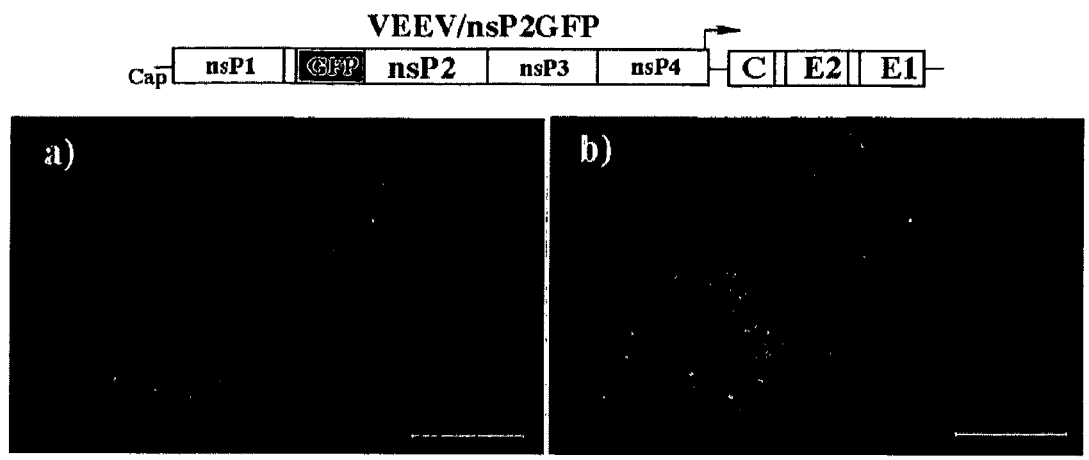
FIG. 16 shows the VEEV nsP2-GFP fusion protein distribution in the cells, infected with VEEV/nsP2GFP. BHK-21 cells were infected with the chimeric virus at an MOI of 20 PFU/cell, and nsP2/GFP distribution was evaluated at 8 h post infection on the confocal microscope. Panel (a) distribution of VEEV nsP2/GFP, (b) overlay of nsP2/GFP and nuclear staining with SYTOX Orange. Images were acquired at 8 h post infection. Bars correspond to 20 mm. The schematic representation of the viral genome is shown.

An infectious VEEV TC-83 variant that contained a GFP insertion in the very amino terminus of nsP2, after aa 3 (FIG. 16) was designed. In spite of normal processing of the nonstructural polyprotein and productive virus replication, the nsP2/GFP, expressed by VEEV/nsP2GFP, was detected only in the cytoplasm of the infected cells.

Figure 8B:
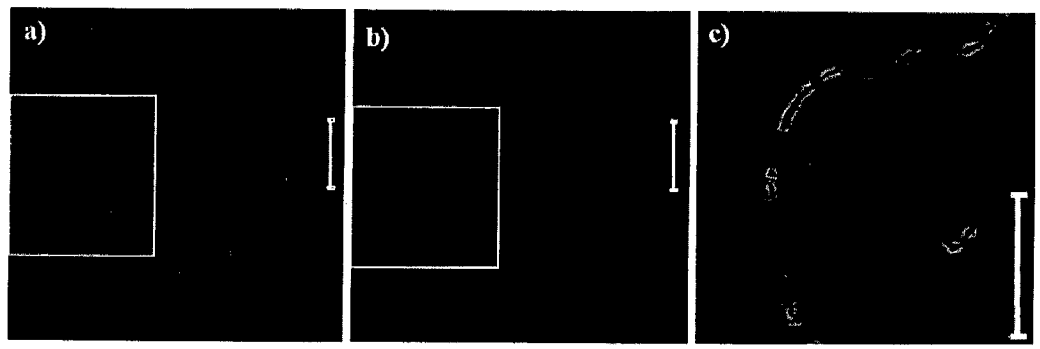
Figure 17A:
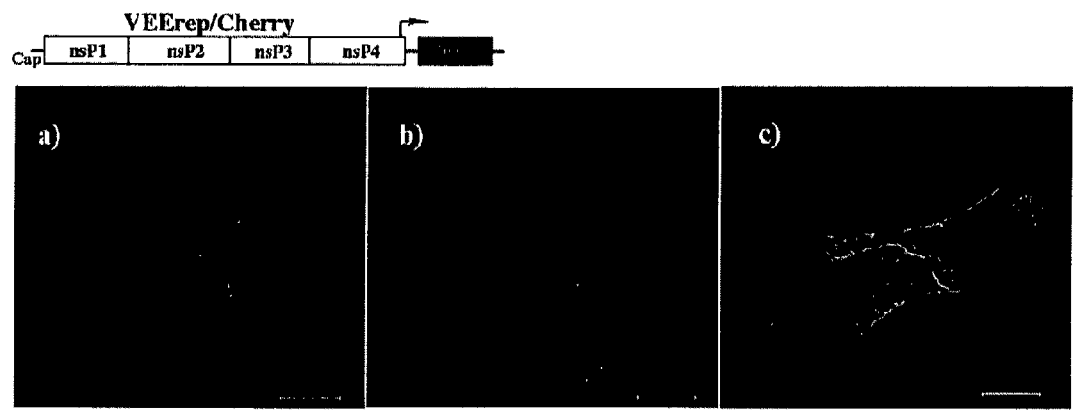
FIG. 17A-17B show the distribution of VEEV nsP2 in the cells infected by the constructs encoding no $C_{VEE}$.
Figure 17B:
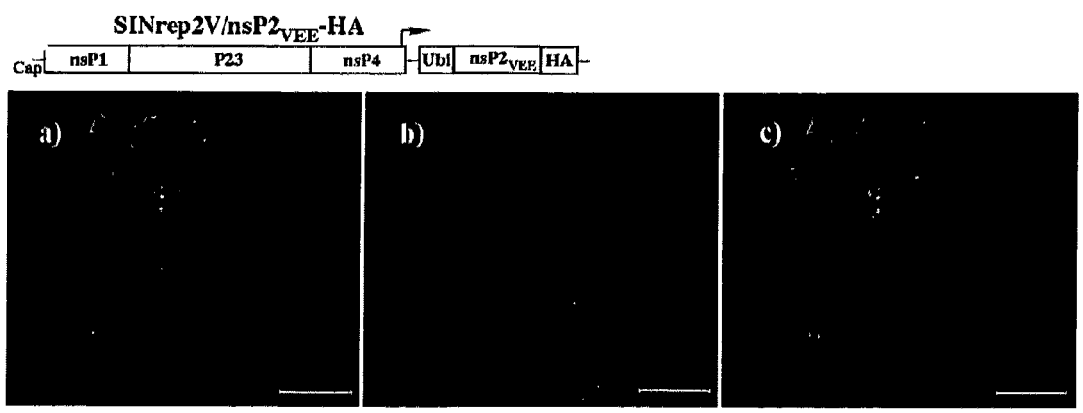

However, the above experiments could not provide a definitive answer to the question of whether VEEV nsP2 itself had not developed an ability for translocation into the nucleus, or whether its cytoplasmic distribution was a result of $C_{VEE}$ function in blocking nuclear import. To distinguish between these possibilities, BHK-21 cells were infected with VEEV replicon, VEErep/Cherry, that did not encode any structural proteins and stained the cells with VEEV nsP2-specific antibodies. Almost all of the nsP2 was detected in the cytoplasm of the replicon-infected cells (FIG. 17A). In another approach, BHK-21 cells were infected with packaged SINV replicon that had a mutation in the nsP2/nsP3 cleavage cite and encoded the HA-tagged VEEV nsP2 under the control of the subgenomic promoter (FIG. 8B). This cleavage cite mutant was incapable of P23 processing, and, thus, the unprocessed SINV nsP2 remained in the cytoplasm and could not interfere with VEEV nsP2 transport into the nucleus. In the cells, infected with SINrep2V/nsP2$_{VEE}$-HA, the HA-tagged nsP2 was also detected only in the cytoplasm (FIG. 17B). Taken together, the results of the experiments strongly suggested that, i) compared to SINV or SFV nsP2, the VEEV-specific counterpart had a dramatically reduced ability for translocation into the nucleus, and ii) its presence in the nuclei at very low concentrations was not only the effect of $C_{VEE}$ functioning in modification of the nucleocytoplasmic traffic, but also a result of the inability of VEEV nsP2 itself for import into the nucleus.

$C_{VEE}$ does not affect nuclear import in mosquito cells. The characteristic feature of alphavirus infection in the mosquito cells is the development of persistent, noncytopathic replication that mirrors the persistent infection in the mosquito vectors. The antiviral response in arthropod cells is different from that in the vertebrate cells, and appears to be not as robust as that in cells of vertebrate origin. Moreover, inhibition of both nuclear import and cellular transcription, likely resulting in development of CPE, could be disadvantageous for persistent virus replication and would have a negative effect on the viability of infected mosquitoes and ultimately virus transmission in nature. Thus, $C_{VEE}$ expression might have no effect on the nuclear import in mosquito cells.

Figure 18A:
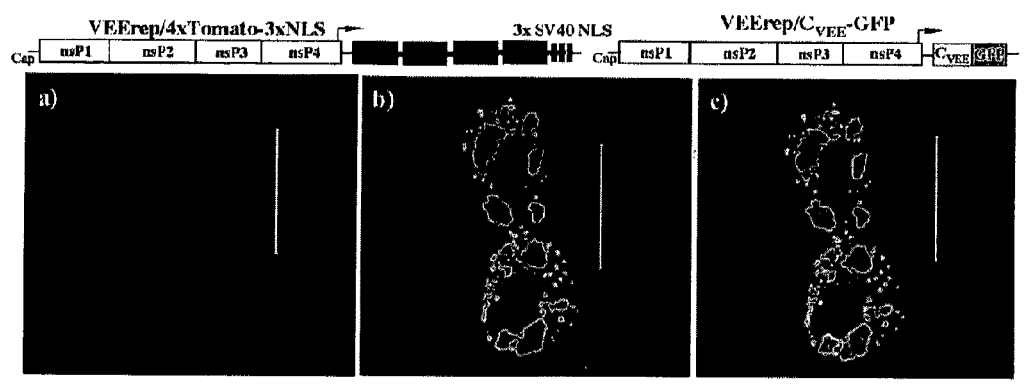
FIG. 18A-18B show that $C_{VEE}$ does not interfere with nuclear import in mosquito cells. $C_{7-10}$ cells were transfected by in vitro-synthesized VEErep/4xTomato-3xNLS and VEErep/$C_{VEE}$-GFP replicon RNAs (A), and VEErep/4xTomato-3xNLS and VEErep/$C_{VEE}$/GFP RNAs (B). Panels include (a) distribution of 4xTomato-3xNLS protein; (b) distribution of $C_{VEE}$-GFP and GFP on (A) and (B), respectively; (c) overlay of two images. All of the images were acquired at 24 h post transfection. Bars correspond to 20 mm. The schematic representation of the replicons is shown on each panel.
Figure 18B:
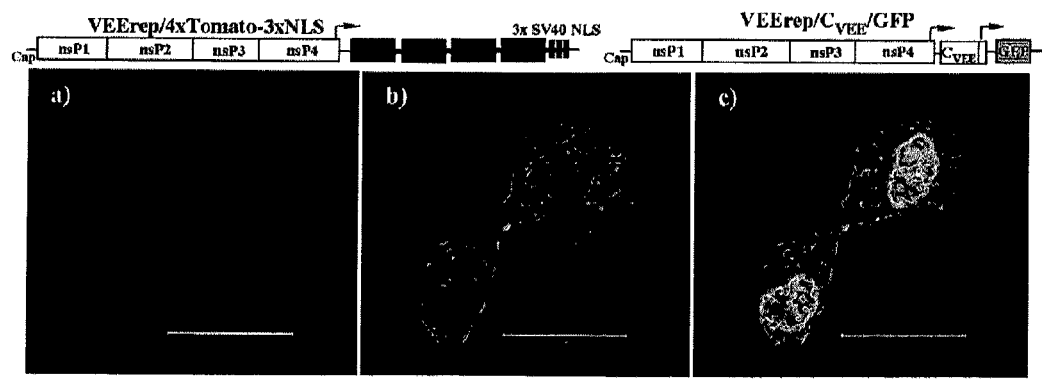

Replicons, packaged into a VEEV TC-83-specific envelope, infected $C_{7-10}$ cells inefficiently, and, therefore, VEErep/4xTomato-3xNLS, VEErep/$C_{VEE}$-GFP and VEErep/$C_{VEE}$/GFP replicon genomes were delivered into these cells by electroporation. Evaluation of the 4xTomato-3xNLS distribution in the $C_{VEE}$-GFP- (FIG. 18A) and $C_{VEE}$-expressing cells (FIG. 18B) strongly indicated that $C_{VEE}$ had no noticeable effect on the translocation of the 4xTomato-3xNLS protein into the cell nuclei. Regardless of the presence of $C_{VEE}$ and $C_{VEE}$-GFP, the 4xTomato-3xNLS was efficiently transported into the nucleus. Thus, this failure to inhibit nuclear import correlates with the inability of the virus to cause CPE and appears to be one of the important determinants of persistent replication in mosquito cells and mosquito vectors.

Discussion

Replication of alphavirus-specific RNAs, translation of the viral proteins, and release of infectious particles do not require a nuclear function. Viral replication can proceed for a long time in the presence of ActD or even in the anucleated cells. Nevertheless, interaction of replicating virus with host cell nuclei plays a critical role in the infectious process and strongly determines pathogenesis on the molecular, cellular and organismal levels. As do other viruses, alphaviruses appear to induce an innate intracellular antiviral response (virus-induced cell response) that is mediated by cellular pathogen recognition receptors (PRRs). The latter response leads to the induction of cell signaling, initiating an antiviral state in the as-yet-uninfected cells and activation of an antiviral reaction in the already infected cells. These processes interfere with productive viral replication and dissemination of the infection. Alphaviruses, in turn, developed mechanisms aimed at strong modification of cell biology and/or development of robust, rapid CPE. In these processes, inhibition of cellular translational and transcriptional machineries appears to play a critical role. These modifications of the intracellular environment are likely to be multicomponent phenomena and determined by different viral nonstructural and structural proteins. The accumulated data strongly indicate that both the Old and New World alphaviruses are capable of downregulating cellular transcription, but utilize very different mechanisms for achieving this goal. The Old World alphavirus-specific nonstructural protein nsP2 is a key player in the inhibition of both cellular messenger and ribosomal RNAs synthesis. This protein causes CPE development, either when being expressed in the context of ns polyprotein, or alone from different expression cassettes. On the other hand, the New World alphaviruses VEEV and EEEV use capsid protein, but not the nsP2, for causing the same phenomenon. This structural protein is distributed both in the cytoplasm and nuclei of the infected cells, and downregulates RNA polymerase I- and II-dependent transcription, and its expression ultimately leads to CPE development. This function of VEEV capsid is determined by a short amino terminal peptide capable of inhibiting transcription even when being fused to other proteins. Modifications of the active peptide in the VEEV genome made virus dramatically less cytopathic and attenuated in vivo without having a strong effect on its replication rates (or no effect at all for some of the constructs).

The distinguishing features of the VEEV capsid-dependent transcriptional shutoff include its slow rates of development and a lack of dependency on the capsid-associated protease activity. These data strongly indicated stoichiometric rather than enzymatic modes of capsid functioning. Moreover, a significant fraction of $C_{VEE}$ was found to be associated with the nuclear membrane and its distribution was reminiscent of that of the nuclear pore complexes. The $C_{VEE}$32-68 peptide fused with GFP demonstrated a similar distribution and was also capable of blocking cellular transcription. Taken together, the results indicated that $C_{VEE}$ (and its active C32-68 peptide) might be involved not only in downregulation of cellular transcription, but also in modification of the NPC and inhibition of nucleocytoplasmic traffic.

The present invention showed the function of several nuclear import pathways, mediated by different importins, and found that all of them were inhibited by the $C_{VEE}$ within 8 h post infection. (Notably, for expression of this protein, the most adequate system, VEEV replicons, was used which express capsid in appropriate cellular compartments and at natural concentrations.) The $C_{VEE}$1-68 peptide, fused with GFP, demonstrated a very similar activity, and $C_{VEE}$frsh-GFP, which does not inhibit cellular transcription and is undetectable in the cell nuclei and on the nuclear membrane, had no effect on the nucleocytoplasmic traffic. Thus, accumulation of $C_{VEE}$ in the nuclear envelope strongly correlated with the inhibition of nuclear import. In infected cells, nucleocytoplasmic traffic is strongly modified, and a great fraction of the newly synthesized cellular proteins is not transported into the nucleus. Among the RNA viruses, blockage of nuclear import is not a new phenomenon. Inhibition of nuclear transport has been described for VSV, poliovirus, rhinovirus and cardiovirus. The VSV matrix protein interacts with the nucleoporin Nup98 and export receptor Rae 1. Thus, M protein accumulates in the NPCs, in which it efficiently inhibits Rae 1-mediated mRNA nuclear export and slows the rate of the nuclear import through the importin a/b1-dependent pathway. Interestingly, VSV also efficiently inhibits cellular transcription, but the correlation between inhibition of nucleocytoplasmic traffic and downregulation of transcription has not been investigated. Two members of the Picornoviridae family, poliovirus and rhinovirus, employ different mechanisms and inhibit nuclear import by degrading the nucleoporins Nup62 and Nup153 by virus-encoded proteases. The same proteases also process the transcription factors. VEEV and, most likely, other New World alphaviruses employ a mechanism that appears to be based on interaction of the capsid protein with NPC. Moreover, functioning of $C_{VEE}$1-68-GFP fusion in inhibition of nuclear import suggests that capsid might function without proteolytic cleavage of the Nups.

The Old World alphaviruses, SINV and SFV, produce capsid proteins that neither block nuclear import, nor interfere with cellular transcription, and do not induce CPE. Consequently, one of the characteristic features of such infection is the accumulation of large amounts of nsP2 in the cell nuclei. The newly described function of $C_{VEE}$ in the inhibition of the nucleocytoplasmic transport suggested that VEEV nsP2 had to be present in the cell nuclei at lower concentration, and unlikely to play an important role in this compartment. Moreover, VEEV nsP2 itself was found to be inefficient in its translocation to the nucleus. It was detected almost exclusively in the cytoplasm not only in the virus-infected cells, but also when produced by VEEV replicon, and expressed from other vectors as GFP-nsP2 or nsP2-HA tag fusions. Such VEEV nsP2 compartmentalization indirectly supports the finding that VEEV replicons, expressing no capsid, caused a less efficient CPE than did similar SINV- and SFV-based constructs and were capable of establishing a persistent replication in the mammalian cells. This was an indication that VEEV- and EEEV-specific nsP2 and other nsPs did not cause as strong, negative effect on cellular biology as did the nsPs of the Old World alphaviruses. Notably, the putative nsP2-specific NLS (that was described in the SFV nsP2) is replaced in VEEV nsP2 by a different aa sequence. This peptide might still function as an NLS, and the mutations in this sequence affect virus and replicon RNA replication. However, as shown for SFV, mutations in this particular peptide could strongly affect the rates of the ns polyprotein processing and/or other nsP2 functions in the RNA replication. Therefore the existence of monopartite NLS in VEEV nsP2 remains questionable. Nevertheless, it is possible that this nonstructural protein, produced by replicating VEEV, has some function in modification of the nucleocytoplasmic traffic because of its recently described interaction with karyopherin 1.

Interestingly, $C_{VEE}$ was found to be incapable of blocking nuclear import in mosquito cells. Large, NLS-containing protein 4xTomato-3xNLS was transported into the cell nuclei regardless of the presence of $C_{VEE}$ in the same cells. Thus, the inability of VEEV capsid to interfere with nucleocytoplasmic trafficking provides a plausible explanation for the noncytopathic phenotype of the VEEV in the mosquito cells. However, this is not the only critical difference between virus replication in the cells of the vertebrate and invertebrate origin.

In conclusion, the present invention demonstrated that i) $C_{VEE}$ efficiently inhibits nuclear import, but does not affect passive diffusion of small proteins; ii) the amino terminal sequence of $C_{VEE}$ interferes with nuclear import as efficiently as does the entire $C_{VEE}$; iii) the capsid protein of the Old World alphavirus, SINV, or $C_{VEE}$ with previously defined frame-shift mutations ($C_{VEE}$frsh), which makes it incapable of transcription inhibition, have no detectable effect on nucleocytoplasmic trafficking; iv) Inhibition of the NPC function is one of the critical mechanisms, which the New World alphaviruses employ for the downregulation of cellular transcription and CPE development. v) $C_{VEE}$ does not noticeably interfere with NPC-mediated nuclear import in the mosquito cells, and this might play a critical role in the ability of the virus to develop a persistent, life-long infection in mosquito vectors.

The following references were cited herein:
1. Aguilar, P. V. et al. 2007, *J Virol* 81:3866-76.
2. Alevizatos, A. C. et al. 1967, *Am J Trop Med Hyg* 16:762-8.
3. Berge, T. O. et al. 1961, *Am. J. Hyg* 73:209-218.
4. Black, B. L. et al. 1993, *J Virol* 67:4814-21.
5. Bredenbeek, P. J. et al. 1993, *J. Virol.* 67:6439-6446.
6. Burke, D. S. et al. 1977, *J Infect Dis* 136:354-359.
7. Choi, H. K. et al. 1991, *Nature* 354:37-43.
8. Faria, P. A. et al. 2005, *Mol Cell* 17:93-102.
9. Frolova, E. I. et al. 2002, *J Virol* 76:11254-11264.
10. Garcia-Tamayo, J. et al. 1979, *J Pathol* 128:87-91.
11. Garmashova, N. et al. 2006, *J Viral* 80:5686-96.
12. Garmashova, N., et al. 2007, *J Virol* 81:2472-84.
13. Gorchakov, R. et al. 2005, *J Viral* 79:9397-409.
14. Griffin, D. 1986. Alphavirus Pathogenesis and Immunity, p. 209-250. In M. Schlesinger (ed.), The Togaviridae and Flaviviridae. Plenum Press, New York.
15. Griffin, D. E. 2001. Alphaviruses, p. 917-962. In D. Knipe and P. Howley (ed.), Fields' Virology, Fourth Edition. Lippincott, Williams and Wilkins, New York.
16. Gustin, K. E. 2003 *Virus Res* 95:35-44.
17. Gustin, K. E., and P. Sarnow. 2001, *Embo J* 20:240-9.
18. Gustin, K. E., and P. Sarnow. 2002, *J Virol* 76:8787-96.
19. Hahn, C. S. et al. 1985, *Proc. Natl. Acad. Sci. USA* 82:4648-4652.
20. Hahn, C. S., and J. H. Strauss. 1990, *J. Viral.* 64:3069-3073.
21. Henderson, B. E. et al. 1971, *Am. J. Epidemiol.* 93:194-205.
22. Imreh, G., and E. Hallberg. 2000, *Exp Cell Res* 259:180-90.
23. Johnson and Martin. 1974, *Adv. Vet. Sci. Comp. Med.* 18:79-116.
24. Kinney, R. M. et al. 1993, *J. Virol.* 67:1269-1277.
25. Kinney, R. M. et al. 1989, *Virology* 170:19-30.
26. Lemm, J. A. et al. 1990, *J. Virol.* 64:3001-3011.
27. Leon, C. A. 1975, *Int J Epidemiol* 4:131-40.
28. Lidsky, P. V. et al. 2006, *J Virol* 80:2705-17.
29. Liljeström, P. et al. 1991, *J. Virol.* 65:4107-4113.
30. Naim, B. et al. 2007, *J Biol Chem* 282:3881-8.
31. Perera, R. et al. 2003, *J Virol* 77:8345-53.
32. Perera, R. et al. 2001, *J Virol* 75:1-10.
33. Petersen, J. M. et al. 2001, *Proc Natl Acad Sci USA* 98:8590-5.
34. Petersen, J. M. et al. 2000, *Mol Cell Biol* 20:8590-601.
35. Petrakova, O. et al. 2005, *J Viral* 79:7597-608.

36. Pittman, P. R. et al. 1996, *Vaccine* 14:337-43.
37. Porter, F. W. et al. 2006, *Proc Natl Acad Sci USA* 103: 12417-22.
38. Rice, C. M. et al. 1987, *J. Virol.* 61:3809-3819.
39. Rice, C. M., and J Strauss 1981, *Proc. Natl. Acad. Sci. USA* 78:2062-2066.
40. Rico-Hesse, R. et al. 1995, *Proc. Natl. Acad. Sci. USA* 92:5278-5281.
41. Rivas, F. et al. 1997, *J Infect Dis* 175:828-32.
42. Strauss, J. H., and E. G. Strauss. 1994, *Microbiol. Rev.* 58:491-562.
43. Takkinen, K. 1986, *Nucleic Acids Res.* 14:5667-5682.
44. Volchkov, V. E. et al. 1991, *Mol. Genet. Mikrobiol. Virusol.* 5:8-15.
45. Volkova, E. et al. 2006, *Virology* 344:315-27.
46. von Kobbe, C. et al. 2000, *Mol Cell* 6:1243-52.
47. Weaver, S.C., and A. D. Barrett. 2004, *Nat Rev Microbiol* 2:789-801.
48. Weaver, S. C. et al. 1994, *J Virol* 68:158-69.
49. Weaver, S. C. et al. 1996, *Lancet* 348:436-40.
50. Wengler, G. et al. 1992, *Virology* 191:880-8.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. An attenuated New World encephalitogenic alphavirus comprising a genome encoding a capsid gene having a deletion corresponding to amino acids 23 to 39 of SEQ ID NO:1.

2. An attenuated New World encephalitogenic alphavirus comprising a genome encoding a capsid gene having a deletion corresponding to amino acids 5 to 39 of SEQ ID NO:1.

3. The attenuated New World encephalitogenic alphavirus of claim 2, further comprising replacement of the amino acids 5 to 39 of SEQ ID NO:1 with an analogous domain from an old world alphavirus capsid protein.

4. The attenuated New World encephalitogenic alphavirus of claim 3, wherein the analogous domain from an Old World alphavirus capsid protein is selected from Sindbis, Semliki Forest, Ross River, or Aura virus.

5. The attenuated New World encephalitogenic alphavirus of claim 2, wherein the New World encephalitogenic alphavirus is Venezuelan equine encephalitis virus (VEEV).

6. An immunogenic composition comprising an attenuated New World encephalitogenic alphavirus of claim 2.

7. A method of stimulating an immune response to an encephalitogenic alphavirus comprising administering to a subject an attenuated New World encephalitogenic alphavirus of claim 2.

8. The attenuated New World encephalitogenic alphavirus of claim 1, further comprising replacement of the amino acids 23 to 39 of SEQ ID NO:1 with an analogous domain from an old world alphavirus capsid protein.

9. The attenuated New World encephalitogenic alphavirus of claim 8, wherein the analogous domain from an Old World alphavirus capsid protein is selected from Sindbis, Semliki Forest, Ross River, or Aura virus.

10. The attenuated New World encephalitogenic alphavirus of claim 1, wherein the New World encephalitogenic alphavirus is Venezuelan equine encephalitis virus (VEEV).

11. A method of stimulating an immune response to an encephalitogenic alphavirus comprising administering to a subject an attenuated New World encephalitogenic alphavirus of claim 1.

* * * * *